United States Patent
Ceppi et al.

(10) Patent No.: US 10,036,071 B2
(45) Date of Patent: Jul. 31, 2018

(54) METHODS FOR THE DETECTION OF SEQUENCE AMPLIFICATION IN THE BRCA1 LOCUS

(71) Applicant: GENOMIC VISION, Bagneux (FR)

(72) Inventors: Maurizio Ceppi, Issy les Moulineaux (FR); Jennifer Abscheidt, Nogent sur Marne (FR); Emmanuel Conseiller, Paris (FR); Etienne Rouleau, Paris (FR)

(73) Assignee: GENOMIC VISION, Bagneux (FR)

( * ) Notice: Subject to any disclaimer, the term of this patent is extended or adjusted under 35 U.S.C. 154(b) by 87 days.

(21) Appl. No.: 14/776,956

(22) PCT Filed: Mar. 14, 2014

(86) PCT No.: PCT/IB2014/000495
§ 371 (c)(1),
(2) Date: Sep. 15, 2015

(87) PCT Pub. No.: WO2014/140788
PCT Pub. Date: Sep. 18, 2014

(65) Prior Publication Data
US 2016/0040249 A1    Feb. 11, 2016

Related U.S. Application Data

(60) Provisional application No. 61/794,731, filed on Mar. 15, 2013.

(51) Int. Cl.
*C12Q 1/68* (2018.01)
*C12Q 1/6886* (2018.01)

(52) U.S. Cl.
CPC ..... *C12Q 1/6886* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| 6,150,514 A | 11/2000 | Swensen |
| 6,582,908 B2 * | 6/2003 | Fodor ............... B01J 19/0046 435/288.3 |
| 2013/0130246 A1 | 5/2013 | Bensimon et al. |

FOREIGN PATENT DOCUMENTS

WO    WO 2013/064895 A1    5/2013

OTHER PUBLICATIONS

Klopocki et al (Annual Reviews Genomics Human Genetics. 2011. 12: 53-72.*
Dermer, G.B. (Bio/Technology (1994) 12: 320.*
International Search Report and Written Opinion dated Aug. 19, 2014 in PCT/IB2014/000495 (submitting English translation only).
Jesús del Valle, et al., "Identification and comprehensive characterization of large genomic rearrangements in the BRCA1 and BRCA2 genes", Breast Cancer Research and Treatment, Springer, vol. 122, XP 19814410A, 2010, pp. 733-743.
Sophie Gad, et al., "Color Bar Coding the BRCA1 Gene on Combed DNA: A Useful Strategy for Detecting Large Gene Rearrangements", Genes, Chromosomes & Cancer, Wiley-Liss, Inc., vol. 31, XP 2512886A, 2001, pp. 75-84.
Kevin Cheeseman, et al., "A Diagnostic Genetic Test for the Physical Mapping of Germline Rearrangements in the Susceptibility Breast Cancer Genes BRCA1 and BRCA2", Human Mutation, Wiley Periodicals, Inc., vol. 33, No. 6, XP 55054668A, 2012, pp. 998-1009.

* cited by examiner

*Primary Examiner* — Carla J Myers
(74) *Attorney, Agent, or Firm* — Oblon, McClelland, Maier & Neustadt, L.L.P.

(57) ABSTRACT

Methods for detecting the amplifications of sequences in the BRCA1 locus, which sequences have ends consisting of or are framed with sequence stretches present at least twice in the BRCA1 locus, and which amplification results in at least two or at least three, especially three, tandem copies of the amplified sequence; methods for determining a predisposition to diseases or disorders associated with these amplifications, including predisposition to ovarian cancer or breast cancer and methods for detecting amplifications with similar features in other loci.

11 Claims, 9 Drawing Sheets

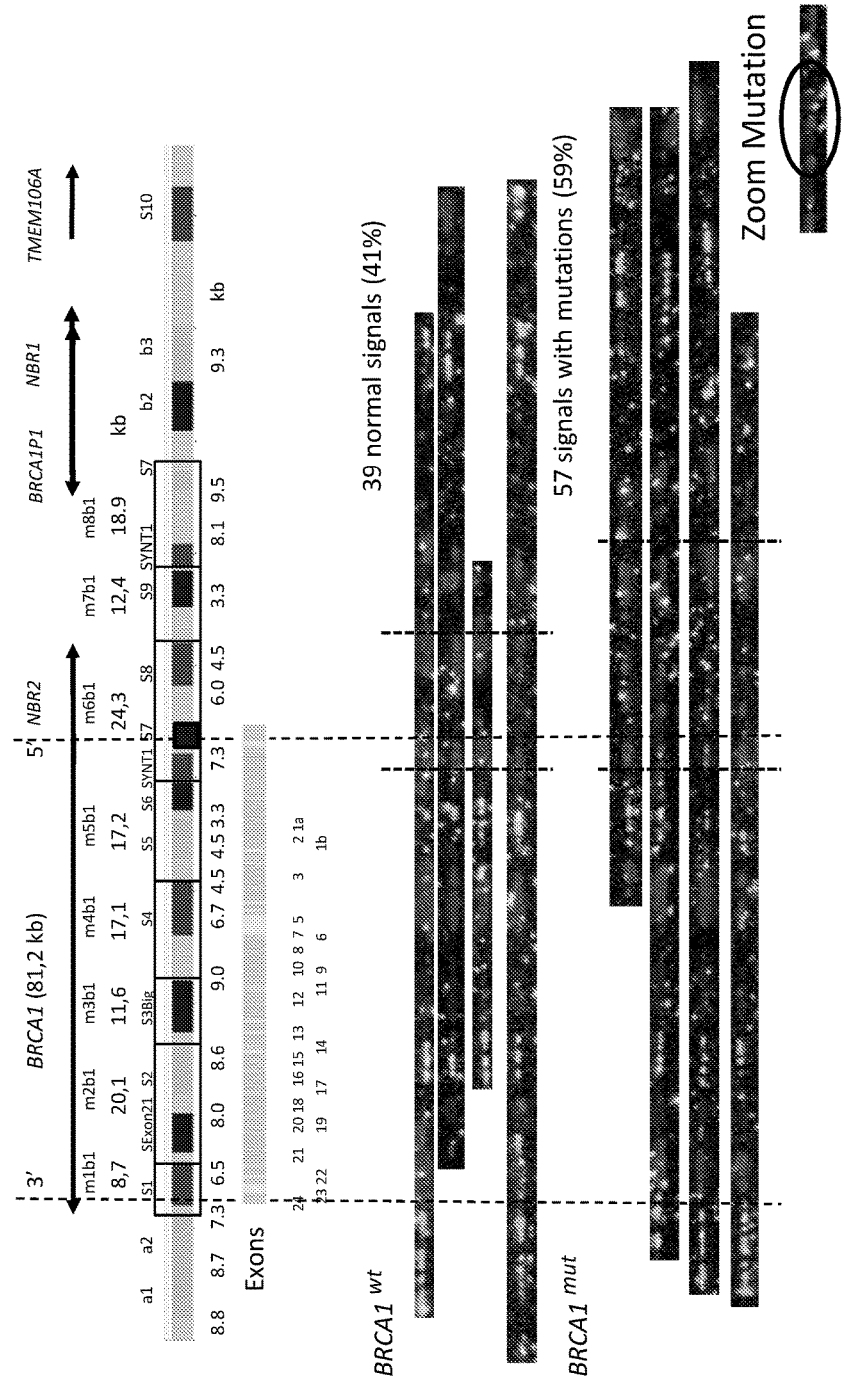

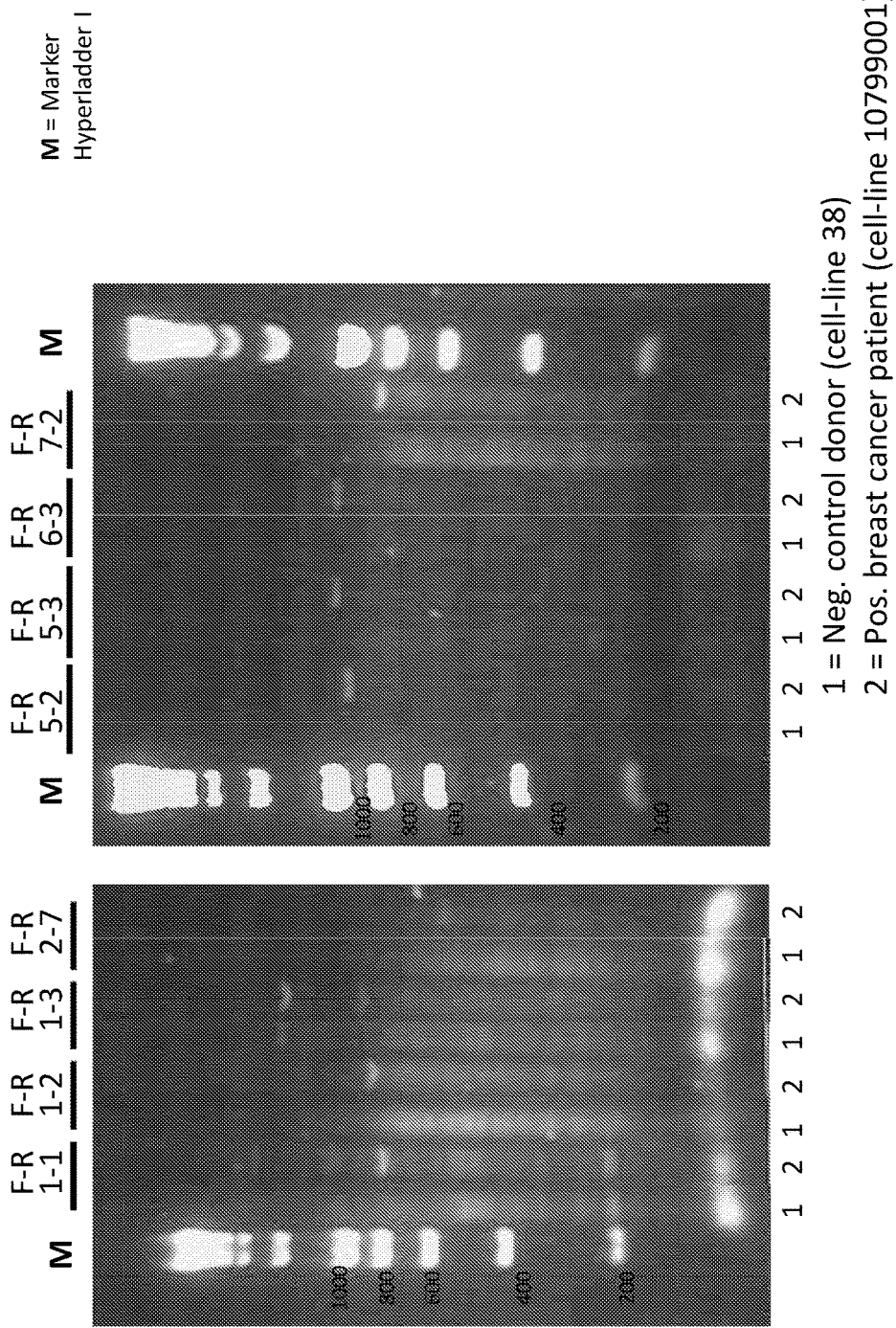

SEQUENCE LISTING

<160> NUMBER OF SEQ ID NOS: 22

<210> SEQ ID NO 1
<211> LENGTH: 4485
<212> TYPE: DNA
<213> ORGANISM: Artificial Sequence
<220> FEATURE:
<223> OTHER INFORMATION: Human - Synt1

<400> SEQUENCE: 1

```
ttcagaaaat acatcaccca agttcccatc cctacctgtc tatccacaaa accaaggcat      60
tcctgagatt agttcattta ttatactaat ataacaagtg tttattaagt atctactact     120
atattcaagt actattctag gagatagaaa tgtagcagtt tacaaaataa agcctgctct     180
catagagctc atattctagt gtggtagaca gttgatacgg aattaaagaa tacatgggaa     240
taagtgcatt aaagagaaaa attaagcagg gtaagggaa acaggtagtt caatatctat      300 gtggggtga gatgtacatg gggggagtca ggaaaggttt cactgaggtg agactagagg      360
atagcttaat aatgtaaaga aacacactat gcaacaatta ggggaagagc attccaagaa     420
agagggagca gagaaggcaa accctgagca ggaccatgcc tgtgtatgca ggacatcaga     480
taggtcaagg tgctaaaatg taataatcca ggaggatatt gtagggaaag actatcagag     540
aggtagctgg taacttctgg taggaaccta taggctattt taaatcttta gctttattct     600
ggtcttttta attttctttt ttttttcag acagagtctc gttctgtcgc ccaggctgga     660
gtgcagtggc accatctcgg ctctctgtaa cctccgcctc ctgaattcaa gtgattctcc     720
tgcctcagcc tcccgagtag ctgggactaa aggcatgcac caccatgcct tggcctccca     780
```

-continued

```
aagtactggg attacaggag tgagccacca tgccagccat cttttttaatt tttaatgtta      840
attaattttt gtagagacag gatctcacta tgatgcccat gctggtcttg aatgcctggc      900
atcaagcaat cttcctgctt cggcttccca aagtgctggg attacaggtg tgagctacta      960
tacccggcct ttagctttct tctgaatgtg aaccttttttt ttttttttg gagatggagt     1020
ctcactcact ctgctgctca ggctggagtg cagtggtgtg gtcttggctc actgcaacct     1080
ctgcctctcg gattgaagtg attcttgtgc ctcagcattc caagtagctg ggactacagg     1140
cgcgtgctgc cacacccggc taatttttt gtattttttgg tagggaaggg gtttcaccat     1200
attgcccagg ctggtcttga agtcctgacc tcaagtgatc catctgcctc gaccgggatt     1260
acaggcgtga gccactacac ttagctctaa atgtgaattt ttgaaacgga tttttttggat   1320
aaagtccagg caagatatca aagaacgact aacctggcag tgtgacaaga atgtggtttt     1380
ttccttaaat atttaacttt ttagaaaagg atcacaaggg ccaggtgcgg tggctcacgc     1440
tgtaatccca gcattttggg aggccaaggc gggccagcct gggtgacaga gaatccatct     1500
caaaaaaga aaaaaaaaa agaaaaggat cacaagaaaa gcttgtggac agtaaccta       1560
ttgtgaaggg ttgtaataca actcttgtaa tcatggggtt tttgacatag cacagggcag     1620
tgaaaagaaa aacaatgaac taagtcagga ggctgggttt ctactaccag ttgtgtatat     1680
aagcagagcc accttgggct aaccactcta cctgaacctg ttttccttctc ttgccattca   1740
ccctgccaga ctccttgggc tattgcaaga ataaaattaa atgctacttg ggaaaatgct     1800
tcacaacctg agatgacttg ggaaaaatgc ttcacaacct gagataactt gtaccaacat     1860
tggtattatt actgggacca aatgtgactt taaaagaaa aacaaccttg acaaagaaaa    1920
ctctgattgg ttactaaatc cctatttctg agataagcta catttcaaag aaattctccg     1980
taaagaaaa attggattca gttatcatac cagatggctt tcattctcac cactgactca     2040
attctgaaac aattatattt cagtatggta attataatct aaactatata aacacactgt     2100
aaacacaaac tttgaacaga tgaaaactcc gatatgtaaa aaggtaatga atgttgaagg     2160
aagactgtga aaagggaaaa gaaaaaaaat taaaatgttc cccttctagg tcctgatgag     2220
agtaaatgtt tactataaaa atgattcaaa tattttaaac acttttcaaa ccaggcaata    2280
ttttaggcct actgtatatt tgcatttttga gcttccaata cggataagtg actggaaaaa    2340
gcagctaggt ttaggttgaa aaacaacaac ccaccgggga acacatttta gcaaattctt     2400
ctgaaagtca aaatgttat agtcataggt aaaaagttac aaagaactac caattgtcag     2460
aaatagctgc caatattgac ttagaagaca gcagaaggaa ttttagttca agaaacctaa     2520
aacaggctga aaaccttacc taccctatag ctaccacaaa taacactgtt tccagtcatg     2580
atcattcctg atcacatatt aagacataac tgcaaattgt gctatactgt actatattaa     2640
aaggaagtga aatatgatcc ctatcctaga acttttccata caaatgaatg taaaacacca   2700
taaaaattaa tcttaaggcc gggcgcggtg gctcacgcct gtaatcccag cactttggga     2760
ggccgaggtg ggcggatcac gaggtcagga agtggagacc atcctggcta acacggtgaa     2820
accccgtctc tactaaaaat acaaaaaatt agccgggcgt ggtggtggac gcctgtagtc    2880
ccagctactt gggggggccga ggcaggagaa tggcgtgaac ccgggaggcg gagcttgcag   2940
tgagccgaga tggcgccact gcactccggc ctgggtgaaa gagcgagact ccgtctcaaa    3000
aacaaaacaa acaaaaatta atcttaagcc aggcgcagtg gctcacgcca gcactttgga    3060
aggccgaggc gggtggatca cgagatcagg acttcaagac cagcctgacc aacgtgatga    3120
```

| | | | | |
|---|---|---|---|---|
| aaccctatct | ctactaaaaa | tacaaaatta | gccggccacg | gtggcgtgcg | cctataatcc | 3180 |
| cagctactca | ggaggctgag | gcaggagaag | cgcttgaact | tgaacctggc | aggcggaggt | 3240 |
| tgcagtgagc | caagatggcg | ccactgcact | ccagcctggg | cgacagagcc | agactccaac | 3300 |
| cccccacccc | gaaaaaaaaa | ggtccaggcc | gggcgcagtg | gctcaggact | gtaatcccag | 3360 |
| cactttggaa | ggctgaggcg | ggtggatcac | aaggtcagga | gatcgagacc | atcttggcta | 3420 |
| acatggtgaa | accccgtctc | tactaaaaat | acaaaaaatt | agccgggcat | agtggtgggc | 3480 |
| gcctgtagtc | ccagctactc | gggaggctga | ggcaggagaa | tggcctgaac | ccgggaggcg | 3540 |
| gagctggcag | tgagccaaga | tcgtgccact | gcactccagc | ctaggcagca | gagcgagacc | 3600 |
| gtgtctcaaa | aaacaaaac | aaaacaaaac | aaaagtctg | ggagcggtgg | ctcacgcctg | 3660 |
| taatcccagc | actttcggag | gccaaggcag | gaggatcacc | tgaggtcagg | agttcgagac | 3720 |
| caacctgacc | aatatggaga | aaccctgtct | ctactaaaaa | tacaaaatta | gctggtgtga | 3780 |
| tggcacatgc | ctgcaatccc | aggtactccg | gaggctgagg | cagcagaatt | gcttgaaccc | 3840 |
| gggaggtgga | ggttgtagtg | agccgagatt | gtgccactgc | actccagcct | gggcaacaag | 3900 |
| agccaaagtc | tgtctcaaaa | aaaaaaaaaa | aaaaaaaaa | agaaattaat | cttaacagga | 3960 |
| aacagaaaaa | agcaatgaaa | agctagaaaa | cataatagtt | gattgaaaat | aacaatttag | 4020 |
| cattttcatt | cttacatctt | taattttat | gtatctgagt | ttttaattga | tggtttaatt | 4080 |
| tgccagaatg | agaaagaaca | tcctattttt | atgactctct | cccatggaaa | tgaaacataa | 4140 |
| atgtatccaa | atgccacact | attgaggatt | ttcctgatca | ctgattgtca | tgagtaagtt | 4200 |
| ttgtgctttt | tcaaaagcag | ttttttccta | caatgtcatt | tcctgcttct | ctggctctga | 4260 |
| ttttcaataa | attgataaat | tgtgaatcct | gttttcctct | tattttgtt | tagctataat | 4320 |
| gttgaagggc | aagggagagg | atggttattt | ataaatcttg | tatcgctctg | aaaacacaac | 4380 |
| atacattttc | cttaatctga | ttaacttgac | ttcaaatatg | aaaaacaact | ttcataaagc | 4440 |
| agaaaagaat | ttacccttt | ttattgtggg | taagaggcaa | tggta | | 4485 |

<210> SEQ ID NO 2
<211> LENGTH: 3309
<212> TYPE: DNA
<213> ORGANISM: Artificial Sequence
<220> FEATURE:
<223> OTHER INFORMATION: Human - S7

<400> SEQUENCE: 2

| | | | | |
|---|---|---|---|---|
| agtttagctc | tgtcgctgga | gttcagtggt | gccatattgg | ctcacagcaa | catctgcctc | 60 |
| ctggttcaag | tgattctcct | gcctcagcct | cctgagtagc | tgggattaca | ggcacatgcc | 120 |
| actacgccca | gctaattttt | gtattttag | tggagagggg | gtttcaccat | gttggccagg | 180 |
| atggtctcga | tctcctgacc | tcgtgatcct | accaccttgg | cctcccaaag | tgctgggatt | 240 |
| acaggcataa | gccaccgccc | tcggcctcat | ccatgatttt | attttgccat | ttcaagtgat | 300 |
| ggagcttgtt | ttagagctgg | aagaaaagcc | aaaatgccag | ttaatctaaa | ctagattcct | 360 |
| gccccagtgc | agaaccaatc | aagacagagt | ccctgtcttt | cccggaccac | aggatttgtg | 420 |
| ttgaaaagga | gaggagtggg | agaggcagag | tggatggaga | acaaggaatc | attttctata | 480 |
| tttttaaagt | tcttcagtta | agaaaatcag | caattacaat | agcctaatct | tactagacat | 540 |
| gtctttttctt | ccctagtatg | taaggtcaat | tctgttcatt | tgcataggag | ataatcatag | 600 |
| gaatcccaaa | ttaatacact | cttgtgctga | cttaccagat | gggacactct | aagattttct | 660 |
| gcatagcatt | aatgacattt | tgtacttctt | caacgcgaag | agcagataaa | tccatttctt | 720 |

```
tctgttccaa tgaactttaa cacattagaa aaacatatat atatatctttt ttaaaaggtt      780 tataaaatga caacttcatt ttatcattttt aaaataaagt aaatttaaga tttggaaggt      840
tttagaataa tacaaaccaa agaactaatg acaacgtcct ttatttttaa agattctaga      900
agttgctttt tgtaattaga caacataaat tctgaattttt ttcacatatt gctgccaacc      960
ccttgggtct tttcctttct ccaagaaaga gaaagctaca gaggagtgac tgaccgggta     1020
ggtggtggta gccttagctt tctccaatgt ttctggttgt tttcttttttc ttgcataaaa     1080 ccaaaatcaa caacgaccaa accaacacca atcaaggcct ccccgcccct aacctttccc     1140
agtgacctgc tctcatctct ggatcctcct caagcacatc cctgccggca gcatctgtta     1200
ctactgacgc tcctctactt ccctcttgcg cttttctcaat ggcgcaaatg gatccagttc     1260
ttaagttctc cctcccacaa aatcctgtct cctcccccttc ccagacatat tcctggcacc     1320
tcttcttcca caaggtccca tcctctcata cataccagcc ggtgtttttt gttttgtttt     1380
gttttgtttt gttttgagac agtctcgctc tgtcgcccag gctggagtgc aatggcgcga     1440
tctcggctca ctgcaacctc cgcctcccgg gttctagcga ttctcctgcc tcagcctcct     1500
gagtagctgg agcggcacca cgcccggcta attttttgtat ttttagtaga gacggagttt     1560
caccacgttg gtcaggctgg tctggaactc ctgacctcat gaccagccga cgttttttaaa     1620 gacatagtgt cccctcaag gcatattcca gttcctatca cgaggattcc cccacggaca     1680
ctcagtgccc ccttcctgat cctcagcgct tccctcgcga cctacaaact gcccccctcc     1740
ccagggttca caacgcctta cgcctctcag gttccgcccc tacccccgt caaagaatac     1800 ccatctgtca gcttcggaaa tccactctcc cacgccagta ccccagagca tcacttgggc     1860
ccctgtcccc tttcccggga ctctactacc tttacccaga gcagagggtg aaggcctcct     1920
gagcgcaggg gcccagttat ctgagaaacc ccacagcctg tcccccgtcc aggaagtctc     1980
agcgagctca cgccgcgcag tcgcagtttt aatttatctg taattcccgc gcttttccgt     2040
tgccacggaa accaaggggc taccgctaag cagcagcctc tcagaatacg aaatcaaggt     2100
acaatcagag gatgggaggg acagaaaagag ccaagcgtct ctcggggctc tggattggcc     2160
acccagtctg cccccggatg acgtaaaagg aaagagacgg aagaggaaga attctacctg     2220
agtttgccat aaagtgcctg ccctctagcc tctactcttc cagttgcggc ttattgcatc     2280
acagtaattg ctgtacgaag gtcagaatcg ctacctattg tccaaagcag tcgtaagaag     2340
aggtcccaat ccccccactct ttccgcccta atggaggtct ccagtttcgg taaatataag     2400
taataaggat tgttgggggg gtggagggaa ataattattt ccagcatgcg ttgcggaatg     2460
aaaggtcttc gccacagtgt tccttagaaa ctgtagtctt atggagagga acatccaata     2520
ccagagcggg cacaattctc acggaaatcc agtggataga ttggagacct gtgcgcgctt     2580
gtacttgtca acagttatgg actggagtgt tatgttttcg tattttgaaa gcagaaacta     2640
ggccttaaaa agatacgtac aactctttag ggagactaca attccatccc agccccagga     2700
gtctggggca agtagtcttg taaggtcagt ggcctgcggg gacgcagtga gcgccgaatt     2760
tgcctggggc aggggaaatg cgctctggcc catgtctgcg cactcgtagt tccacccctc     2820
agccccagtg tttgttattt ttcgggttca gcttgctttt gccccgtctc cgtcgacgca     2880
atcgccacca gtcaatgggg tggtcgtttt gagggacaag tggtaagagc caatcttctt     2940
ggcgaaaacg cggagaaacg ggactagtta ctgtctttgt ccgccatgtt agattcaccc     3000
cacagagata gcggcagagc tggcagcgga cggtctttgc attgccgcct ccccagggg     3060
```

-continued

```
cgggaagctg gtaaggaagc agcctgggtt agctaggggt ggggtcacgt cacactaaga    3120
gggtttggag aagttcaagg gaggaatcct gcaaagaaga gggcgacttt tttccgtgtc    3180
tccggacagc taatcgtttt agtgacagga tgagagagcc cttcgtgttc tgagggaccg    3240
agtgggcgaa aagcgccgga gagttggaga gtctgtggtt cagaatgcga ggtgacaacg    3300
tgctagcag                                                           3309
```

<210> SEQ ID NO 3
<211> LENGTH: 20
<212> TYPE: DNA
<213> ORGANISM: Artificial Sequence
<220> FEATURE:
<223> OTHER INFORMATION: Human - F7

<400> SEQUENCE: 3
agggtttcat cacgttggtc                                               20

<210> SEQ ID NO 4
<211> LENGTH: 20
<212> TYPE: DNA
<213> ORGANISM: Artificial Sequence
<220> FEATURE:
<223> OTHER INFORMATION: Human - R7

<400> SEQUENCE: 4
gcaaatgtag tggggacttg                                               20

<210> SEQ ID NO 5
<211> LENGTH: 18
<212> TYPE: DNA
<213> ORGANISM: Artificial Sequence
<220> FEATURE:
<223> OTHER INFORMATION: Human - F9

<400> SEQUENCE: 5
ctgcgcctgg cttaagat                                                 18

<210> SEQ ID NO 6
<211> LENGTH: 18
<212> TYPE: DNA
<213> ORGANISM: Artificial Sequence
<220> FEATURE:
<223> OTHER INFORMATION: Human - R8

<400> SEQUENCE: 6
gatgtgggtg gggtcaga                                                 18

<210> SEQ ID NO 7
<211> LENGTH: 22
<212> TYPE: DNA
<213> ORGANISM: Artificial Sequence
<220> FEATURE:
<223> OTHER INFORMATION: Human - F1

<400> SEQUENCE: 7
atagggtttc atcacgttgg tc                                            22

<210> SEQ ID NO 8
<211> LENGTH: 20
<212> TYPE: DNA
<213> ORGANISM: Artificial Sequence
<220> FEATURE:
<223> OTHER INFORMATION: Human - R1

<400> SEQUENCE: 8

```
ctaatctggt gggcacttgg                                              20

<210> SEQ ID NO 9
<211> LENGTH: 22
<212> TYPE: DNA
<213> ORGANISM: Artificial Sequence
<220> FEATURE:
<223> OTHER INFORMATION: Human - F2

<400> SEQUENCE: 9
gtcttgaagt cctgatctcg tg                                           22

<210> SEQ ID NO 10
<211> LENGTH: 20
<212> TYPE: DNA
<213> ORGANISM: Artificial Sequence
<220> FEATURE:
<223> OTHER INFORMATION: Human - R2

<400> SEQUENCE: 10
gtgtctagct tggggtttgg                                              20

<210> SEQ ID NO 11
<211> LENGTH: 22
<212> TYPE: DNA
<213> ORGANISM: Artificial Sequence
<220> FEATURE:
<223> OTHER INFORMATION: Human - F3

<400> SEQUENCE: 11
gagatagggt ttcatcacgt tg                                           22

<210> SEQ ID NO 12
<211> LENGTH: 20
<212> TYPE: DNA
<213> ORGANISM: Artificial Sequence
<220> FEATURE:
<223> OTHER INFORMATION: Human - R3

<400> SEQUENCE: 12
cagatgggga cttggaaaac                                              20

<210> SEQ ID NO 13
<211> LENGTH: 20
<212> TYPE: DNA
<213> ORGANISM: Artificial Sequence
<220> FEATURE:
<223> OTHER INFORMATION: Human - F4

<400> SEQUENCE: 13
gtttcatcac gttggtcagg                                              20

<210> SEQ ID NO 14
<211> LENGTH: 20
<212> TYPE: DNA
<213> ORGANISM: Artificial Sequence
<220> FEATURE:
<223> OTHER INFORMATION: Human - R4

<400> SEQUENCE: 14
ctgagtcaga tggggacttg                                              20

<210> SEQ ID NO 15
<211> LENGTH: 21
<212> TYPE: DNA
```

```
<213> ORGANISM: Artificial Sequence
<220> FEATURE:
<223> OTHER INFORMATION: Human - F5

<400> SEQUENCE: 15
gttcaagttc aagcgcttct c                                             21

<210> SEQ ID NO 16
<211> LENGTH: 20
<212> TYPE: DNA
<213> ORGANISM: Artificial Sequence
<220> FEATURE:
<223> OTHER INFORMATION: Human - F6

<400> SEQUENCE: 16
ctgccaggtt caagttcaag                                               20

<210> SEQ ID NO 17
<211> LENGTH: 25
<212> TYPE: DNA
<213> ORGANISM: Artificial Sequence
<220> FEATURE:
<223> OTHER INFORMATION: Primer Synt1-F

<400> SEQUENCE: 17
ttcagaaaat acatcaccca agttc                                         25

<210> SEQ ID NO 18
<211> LENGTH: 22
<212> TYPE: DNA
<213> ORGANISM: Artificial Sequence
<220> FEATURE:
<223> OTHER INFORMATION: Primer Synt1-R

<400> SEQUENCE: 18
taccattgcc tcttacccac aa                                            22

<210> SEQ ID NO 19
<211> LENGTH: 21
<212> TYPE: DNA
<213> ORGANISM: Artificial Sequence
<220> FEATURE:
<223> OTHER INFORMATION: Primer S7-F

<400> SEQUENCE: 19
gagtttagct ctgtcgctgg a                                             21

<210> SEQ ID NO 20
<211> LENGTH: 20
<212> TYPE: DNA
<213> ORGANISM: Artificial Sequence
<220> FEATURE:
<223> OTHER INFORMATION: Primer S7-R

<400> SEQUENCE: 20
tgctagcacg ttgtcacctc                                               20

<210> SEQ ID NO 21
<211> LENGTH: 48
<212> TYPE: DNA
<213> ORGANISM: Artificial Sequence
<220> FEATURE:
<223> OTHER INFORMATION: Breakpoint 48bp

<400> SEQUENCE: 21
gaggcaggag aatggcgtga acccgggagg cggagcttgc agtgagcc                48
```

<210> SEQ ID NO 22
<211> LENGTH: 18000
<212> TYPE: DNA
<213> ORGANISM: Homo sapiens

<400> SEQUENCE: 22

| | | | | | |
|---|---|---|---|---|---|
| atagaaactg | gtatcaggtc | ctttcctgtc | ttcacaatga | ttacaaagcg | ggcaaacact | 60 |
| gacccttaga | aggggggaatg | cataaggata | tgcagaaatg | aacagaaagg | agaaactggg | 120 |
| aaggctcaaa | cacaatgtgc | ttatttcaaa | actgcttgca | gtttgctttc | actgatggac | 180 |
| acaaaaaata | caaaacactg | ttcaaaatga | tgttacatcc | taatagataa | tatatgtcag | 240 |
| tcgggtgtgg | tggctcacgc | ctgtaatccc | agaactttgg | gaggccgagg | caggtggatc | 300 |
| acaaggtcag | gagttcgaga | ccagcctggc | caatatggtg | aaaccttatc | tctactaaaa | 360 |
| gtacaaaaat | tagccaagca | tggtggcggg | tgcctgtagt | cccagctacc | tgggaggctg | 420 |
| aggtagaaga | atcgcttgaa | ctcgggggc | ggaggttgca | gtgagccaag | atcatgccac | 480 |
| tgcactccag | cctgggcgac | agagcgagac | tttgtctcaa | aaaaaaaaa | aaagataata | 540 |
| tatgtcaaaa | ctttaccagg | aactatgatt | acaaccaact | tttgataact | atatactctc | 600 |
| tgagaaagaa | tgaaatggag | ttggattttt | cgttctcact | taattgaaga | agtaaagct | 660 |
| tctataaagt | taggtgtttc | ctgggttatg | aaggacaaaa | acaaaagcta | ataatggagc | 720 |
| cacataacac | attcaaactt | acttgcaaaa | tatgtggtca | cactttgtgg | agacaggttc | 780 |
| cttgatcaac | tccagactag | cagggtaggg | ggggagaaaa | agaaaataaa | tgaggctcaa | 840 |
| taatttattt | aaaaataaag | ctattcttag | tgaataagtt | caactttgag | ctgttatgac | 900 |
| tgagtcaaca | taaggcctca | agttcgttca | atatttatta | aatgtctgct | gtgtcaggaa | 960 |
| ctgagaatac | agcagagaat | acgatcctta | ccttcagtga | gctttcagat | atcaaaacag | 1020 |
| aattatattg | atcccttcaa | tactctatac | tatcatcagc | atttaaaaga | ttagttgata | 1080 |
| atagttcgta | cgaattcatt | tccagtgata | tattttttctg | cactatcact | gtgggtgcac | 1140 |
| atctcatctt | taagctccat | aaagacaaaa | ttttctgctt | atatttcttt | tgaattcctt | 1200 |
| cctagaactt | ttttttgttt | actgtaaatg | cctttttaac | ttaatatgga | aaatttcaag | 1260 |
| tatttcaaaa | tttcaagtaa | ataaaataat | aaaatgaact | atatggacca | tcaccctggt | 1320 |
| ccaacaacca | tcaactcatg | gccaagctgt | ttcacccata | tccaccccta | ccccagatta | 1380 |
| ttttaattat | tattactttt | aagataaggt | cacactctgt | cacctaggct | ggagtgcagt | 1440 |
| ggtgcaaaca | tacctcactg | cagccttgaa | ctcctgggct | caagcaatcc | tcccagcacg | 1500 |
| gggtttacag | gcatgagcca | acacacccaa | acccaagtgt | cttctttttt | ttgagatggg | 1560 |
| gttttgcttt | tgtagcccag | actggcatgc | aatggtgcga | tctcggctca | ctgcaacctc | 1620 |
| tgcctcccaa | gttcaagtga | ttctcctgcc | tcagcctccc | aggtagttgg | aactacaggc | 1680 |
| gtgcgccacc | acgcccggct | gattttttcgt | attttttagta | gagttggggt | ttcaccatgt | 1740 |
| tggccggctg | gtcttgaact | cctgacctca | ggtgatccgc | ctgccttggc | ctcccaaagt | 1800 |
| gctgggatta | caggtgtgag | ccaccatgcc | cagccccaag | tgtcttctga | tctataggtg | 1860 |
| tctcttactt | tttctccctt | gtcatttatt | tttaaaatta | ggtcatttga | cctgtggagt | 1920 |
| ttcccccatt | ctggattttg | ctgattgtat | aaccctatgg | tgaggtttaa | cttgttcctc | 1980 |
| tagccttatt | tcctataaac | tagacttaca | ggcttaatca | ttcaggttca | actttctggc | 2040 |
| aagaacactt | tacagatggt | actgtgtact | cttattagat | cacttcagaa | gaggcatgat | 2100 |

```
gtttggttg  tgattacttt  gtaaaaacag  tgtaataagt  actcactaaa  ggaaatttag    2160
aaaatgataa  gcttaaggcc  gggcatggtg  cctcatgcct  gtaatcctag  cactttggga    2220
ggctgaggtg  ggtggatcac  ctgagctcag  gagttccaga  tcatcctgga  caatatggtg    2280
aaaccctgtc  tacgctaaaa  atacaaaaat  tagccgggcg  tggtggcgca  tgcctgtggt    2340
ctcagctact  ttggagacta  aggtagaagg  atcacttgaa  tcctggaggt  ggaggttgca    2400
gagtgagcca  atatcgtgcc  actgcactcc  agcctaggtg  acagaggaag  actctgtctc    2460
aaaaaaaaga  aataaggcc  agacacgggg  gctcatgctt  gtaatcccag  cacttgggag    2520
gccgaggcgg  gcggatcatg  aggtcaggat  ttcgagacca  gcctggccaa  cacagtgaaa    2580
cgctgtctct  actaaaaata  ccaaaactaa  ctgggcatgg  tggcatgcgc  ctgtaatccc    2640
agctacttgg  gaggctaagg  caggagaatc  gcttgaaccg  ggaagtgca  cgttgcagtg    2700 agccaagatc  gcgccactgt  actccaacct  gggcgacaga  gctggactcc  atctcaaaat    2760
aataataagc  ttaaaaataa  aaacttcaga  aaatacatca  cccaagttcc  catccctacc    2820
tgtctatcca  caaaaccaag  gcattcctga  gattagttca  tttattatac  taatataaca    2880 agtgttatt  aagtatctac  tactatattc  aagtactatt  ctaggagata  gaaatgtagc    2940
agtttacaaa  ataaagcctg  ctctcataga  gctcatattc  tagtgtggta  gacagttgat    3000
acggaattaa  agaatacatg  ggaataagtg  cattaaagag  aaaattaag  cagggtaagg    3060 ggaaacaggt  agttcaatat  ctatgtgggg  gtgagatgta  catgggggga  gtcaggaaag    3120
gtttcactga  ggtgagacta  gaggatagct  taataatgta  agaaacaca  ctatgcaaca    3180 attaggggaa  gagcattcca  agaaagaggg  agcagagaag  gcaaaccctg  agcaggacca    3240
tgcctgtgta  tgcaggacat  cagataggtc  aaggtgctaa  aatgtaataa  tccaggagga    3300
tattgtaggg  aaagactatc  agagaggtag  ctggtaactt  ctggtaggaa  cctataggct    3360
attttaaatc  tttagcttta  ttctggtctt  tttaattttc  tttttttttt  tcagacagag    3420
tctcgttctg  tcgcccaggc  tggagtgcag  tggcaccatc  tcggctctct  gtaacctccg    3480
cctcctgaat  tcaagtgatt  ctcctgcctc  agcctcccga  gtagctggga  ctaaaggcat    3540
gcaccaccat  gccttggcct  cccaaagtac  tgggattaca  ggagtgagcc  accatgccag    3600
ccatcttttt  aattttaat  gttaattaat  ttttgtagag  acaggatctc  actatgatgc    3660
ccatgctggt  cttgaatgcc  tggcatcaag  caatcttcct  gcttcggctt  cccaaagtgc    3720
tgggattaca  ggtgtgagct  actataccg  gcctttagct  ttcttctgaa  tgtgaacctt    3780
tttttttttt  tttggagatg  gagtctcact  cactctgctg  ctcaggctgg  agtgcagtgg    3840
tgtggtcttg  gctcactgca  acctctgcct  ctcggattga  agtgattctt  gtgcctcagc    3900
attccaagta  gctgggacta  caggcgcgtg  ctgccacacc  cggctaattt  ttttgtattt    3960
ttggtaggga  aggggtttca  ccatattgcc  caggctggtc  ttgaagtcct  gacctcaagt    4020
gatccatctg  cctcgaccgg  gattacaggc  gtgagccact  acacttagct  ctaaatgtga    4080
atttttgaaa  cggatttttt  ggataaagtc  caggcaagat  atcaaagaac  gactaacctg    4140
gcagtgtgac  aagaatgtgg  ttttttcctt  aaatatttaa  cttttagaa  aaggatcaca    4200 agggccaggt  gcgtggctc  acgctgtaat  cccagcattt  tgggaggcca  aggcgggcca    4260
gcctgggtga  cagagaatcc  atctcaaaaa  aagaaaaaa  aaaagaaaa  ggatcacaag    4320 aaaagcttgt  ggacagtaac  cttattgtga  agggttgtaa  tacaactctt  gtaatcatgg    4380 ggttttgac  atagcacagg  gcagtgaaaa  gaaaacaat  gaactaagtc  aggaggctgg    4440
gtttctacta  ccagttgtgt  atataagcag  agccaccttg  ggctaaccac  tctacctgaa    4500
```

```
cctgtttcct tctcttgcca ttcaccctgc cagactcctt gggctattgc aagaataaaa    4560
ttaaatgcta cttgggaaaa tgcttcacaa cctgagatga cttgggaaaa atgcttcaca    4620
acctgagata acttgtacca acattggtat tattactggg accaaatgtg actttaaaaa    4680
gaaaaacaac cttgacaaag aaaactctga ttggttacta aatccctatt tctgagataa    4740
gctacatttc aaagaaattc tccgtaaaag aaaaattgga ttcagttatc ataccagatg    4800
gctttcattc tcaccactga ctcaattctg aaacaattat atttcagtat ggtaattata    4860
atctaaacta tataaacaca ctgtaaacac aaactttgaa cagatgaaaa ctccgatatg    4920
taaaaaggta atgaatgttg aaggaagact gtgaaagggg aaaagaaaaa aaattaaaat    4980
gttccccttc taggtcctga tgagagtaaa tgtttactat aaaaatgatt caaatatttt    5040
aaacactttt caaaccaggc aatattttag gcctactgta tatttgcatt ttgagcttcc    5100
aatacggata agtgactgga aaagcagct aggtttaggt tgaaaaacaa caacccaccg    5160
gggaacacat tttagcaaat tcttctgaaa gtcaaaaatg ttatagtcat aggtaaaaag    5220
ttacaaagaa ctaccaattg tcagaaatag ctgccaatat tgacttagaa gacagcagaa    5280
ggaattttag ttcaagaaac ctaaaacagg ctgaaaacct tacctaccct atagctacca    5340
caaataacac tgtttccagt catgatcatt cctgatcaca tattaagaca taactgcaaa    5400
ttgtgctata ctgtactata ttaaaaggaa gtgaaatatg atccctatcc tagaactttc    5460
catacaaatg aatgtaaaac accataaaaa ttaatcttaa ggccgggcgc ggtggctcac    5520
gcctgtaatc ccagcacttt gggaggccga ggtgggcgga tcacgaggtc aggaagtgga    5580
gaccatcctg gctaacacgg tgaaaccccg tctctactaa aaatacaaaa aattagccgg    5640
gcgtggtggt ggacgcctgt agtcccagct acttgggggg ccgaggcagg agaatggcgt    5700
gaacccggga ggcggagctt gcagtgagcc gagatggcgc cactgcactc cggcctgggt    5760
gaaagagcga gactccgtct caaaaacaaa acaaacaaaa attaatctta agccaggcgc    5820
agtggctcac gccagcactt tggaaggccg aggcgggtgg atcacgagat caggacttca    5880
agaccagcct gaccaacgtg atgaaaccct atctctacta aaaatacaaa attagccggc    5940
cacggtggcg tgcgcctata atcccagcta ctcaggaggc tgaggcagga aagcgcttg     6000 aacttgaacc tggcaggcgg aggttgcagt gagccaagat ggcgccactg cactccagcc    6060
tgggcgacag agccagactc caaccccccca ccccgaaaaa aaaaggtcca ggccgggcgc    6120
agtggctcag gactgtaatc ccagcacttt ggaaggctga ggcgggtgga tcacaaggtc    6180
aggagatcga gaccatcttg gctaacatgg tgaaaccccg tctctactaa aaatacaaaa    6240
aattagccgg gcatagtggt gggcgcctgt agtcccagct actcgggagg ctgaggcagg    6300
agaatggcct gaacccggga ggcggagctg cagtgagcc aagatcgtgc cactgcactc    6360
cagcctaggc agcagagcga gaccgtgtct caaaaaaaca aaacaaaaca aacaaaaag    6420 tctgggagcg tggctcacg cctgtaatcc cagcactttc ggaggccaag gcaggaggat    6480
cacctgaggt caggagttcg agaccaacct gaccaatatg gagaaaccct gtctctacta    6540
aaaatacaaa attagctggt gtgatggcac atgcctgcaa tcccaggtac tccggaggct    6600
gaggcagcag aattgcttga acccgggagg tggaggttgt agtgagccga gattgtgcca    6660
ctgcactcca gcctgggcaa caagagccaa agtctgtctc aaaaaaaaaa aaaaaaaaa     6720 aaaaagaaat taatcttaac aggaaacaga aaaaagcaat gaaaagctag aaaacataat    6780
agttgattga aaataacaat ttagcatttt cattcttaca tctttaattt ttatgtatct    6840
```

```
gagtttttaa ttgatggttt aatttgccag aatgagaaag aacatcctat ttttatgact    6900
ctctcccatg gaaatgaaac ataaatgtat ccaaatgcca cactattgag gattttcctg    6960
atcactgatt gtcatgagta agttttgtgc tttttcaaaa gcagtttttt cctacaatgt    7020
catttcctgc ttctctggct ctgattttca ataaattgat aaattgtgaa tcctgttttc    7080
ctcttatttt tgtttagcta taatgttgaa gggcaaggga gaggatggtt atttataaat    7140
cttgtatcgc tctgaaaaca caacatacat tttccttaat ctgattaact tgacttcaaa    7200
tatgaaaaac aactttcata aagcagaaaa gaatttaccc ttttttattg tgggtaagag    7260
gcaatggtac aactttcaa cttattttt gaatgttact cactactaac catcaccata    7320
tttaaaaaaa ttaaagaact aatttagttt agtttattat ttatttgaca aatgtttatt    7380
gagtggcaac taggtcccaa gtaccgttct aactactgaa catacagatg tatgtaaaca    7440
aaacaaaaat cccatcctgg agtttacatt ctgtgggact agagataaaa aatggataca    7500
ttacatagaa tgtcagctag taatcagtgt tatggagaag cagcaggaat agaagataaa    7560
gtgtgtgctg ggggtgtggt aatttaaat aggggtgtct ggaaatgaaa aggtggtatt    7620
tcaatcaaga ttttagacc atggctgggt gcaatggctc aggcctgtaa tcccagcacc    7680
ttgagaggcc aagggagggt agatcacttg aggtcaggag tttgagacca gcatggccaa    7740
catagcaaaa ccctatctct acaacagaaa aatacaagaa tggctggacg cagtggctta    7800
tgcctgtaat cctagcactt gggaggccc aggcgggtgg atcacaaggt caggagatca    7860
agactatcct ggctaacacg gtgaaatccc gcctctacta aaaagaaaa aaaaatacaa    7920
aaaattagcc gggcgtggta gtgggtgctt gtagtcccag ctattcagga ggctcaggca    7980
gaagaatggc atgaacccgg gaggcagagt tgcagtgag ctgagatcgc gccactgcac    8040
tccagcctgg gcaacagagc aagactccat ctcaaaaaaa gaaaaaaaa tacaaaaatt    8100
agctgggcat ggtggtgcac acctatcgtc cctgctactc tggaggctga ggtgggagga    8160
ttgcttgagc ctgacgaggt tgaggctgca gtgagctgtg atagcaccac tgcactccag    8220
cctctcgaca gagatcctat ataaaaaaaa aacctctgca tttcattgta tgtaaataag    8280
tatgtaattt cattgtatgt acagagccag tttcaaacaa aggttcttcc aaataccat    8340
cctctcaacg acaccgatca tccatgtttt ttttttttt tttttttttt tgagatggag    8400
tttagctctg tcgctggagt tcagtggtgc catattggct cacagcaaca tctgcctcct    8460
ggttcaagtg attctcctgc ctcagcctcc tgagtagctg ggattacagg cacatgccac    8520
tacgcccagc taattttgt attttagtg gagaggggt ttcaccatgt tggccaggat    8580
ggtctcgatc tcctgacctc gtgatcctac caccttggcc tcccaaagtg ctgggattac    8640
aggcataagc caccgccctc ggcctcatcc atgattttat tttgccattt caagtgatgg    8700
agcttgtttt agagctggaa gaaaagccaa aatgccagtt aatctaaact agattcctgc    8760
cccagtgcag aaccaatcaa gacagagtcc ctgtctttcc cggaccacag gatttgtgtt    8820
gaaaaggaga ggagtgggag aggcagagtg gatggagaac aaggaatcat tttctatatt    8880
tttaaagttc ttcagttaag aaaatcagca attacaatag cctaatctta ctagacatgt    8940
cttttcttcc ctagtatgta aggtcaattc tgttcatttg cataggagat aatcatagga    9000
atcccaaatt aatacactct tgtgctgact taccagatgg gacactctaa gatttctgc    9060
atagcattaa tgcatttgg tacttcttca acgcgaagag cagataaatc catttctttc    9120
tgttccaatg aactttaaca cattagaaaa acatatatat atatcttttt aaaggttta    9180
taaaatgaca acttcatttt atcatttaa aataaagtaa atttaagatt tggaaggttt    9240
```

```
tagaataata caaaccaaag aactaatgac aacgtccttt attttttaaag attctagaag   9300 ttgcttttg taattagaca acataaattc tgaattttt cacatattgc tgccaacccc     9360
ttgggtcttt tcctttctcc aagaaagaga aagctacaga ggagtgactg accgggtagg   9420
tggtggtagc cttagctttc tccaatgttt ctggttgttt tcttttcctt gcataaaacc   9480
aaaatcaaca acgaccaaac caacaccaat caaggcctcc ccgcccctaa cctttcccag   9540
tgacctgctc tcatctctgg atcctcctca agcacatccc tgccggcagc atctgttact   9600
actgacgctc ctctacttcc ctcttgcgct ttctcaatgg cgcaaatgga tccagttctt   9660
aagttctccc tcccacaaaa tcctgtctcc tccccttccc agacatattc ctggcacctc   9720
ttcttccaca aggtcccatc ctctcataca taccagccgg tgttttttgt tttgtttttgt  9780 tttgttttgt tttgagacag tctcgctctg tcgcccaggc tggagtgcaa tggcgcgatc   9840
tcggctcact gcaacctccg cctcccgggt tctagcgatt ctcctgcctc agcctcctga   9900
gtagctggag cggcaccacg cccggctaat ttttgtattt ttagtagaga cggagttttca  9960 ccacgttggt caggctggtc tggaactcct gacctcatga ccagccgacg ttttttaaaga 10020 catagtgtcc ccctcaaggc atattccagt tcctatcacg aggattcccc cacgacact    10080 cagtgccccc ttcctgatcc tcagcgcttc cctcgcgacc tacaaactgc cccctcccc   10140 agggttcaca acgccttacg cctctcaggt tccgcccccta ccccccgtca agaatacccc  10200
atctgtcagc ttcggaaatc cactctccca cgccagtacc ccagagcatc acttgggccc  10260
cctgtccctt tcccgggact ctactacctt tacccagagc agagggtgaa ggcctcctga  10320 gcgcagggc ccagttatct gagaaacccc acagcctgtc cccgtccag gaagtctcag    10380 cgagctcacg ccgcgcagtc gcagttttaa tttatctgta attcccgcgc ttttccgttg  10440
ccacggaaac caaggggcta ccgctaagca gcagcctctc agaatacgaa atcaaggtac  10500
aatcagagga tgggagggac agaaagagcc aagcgtctct cggggctctg gattggccac  10560
ccagtctgcc cccggatgac gtaaaaggaa agagacggaa gaggaagaat tctacctgag  10620
tttgccataa agtgcctgcc ctctagcctc tactcttcca gttgcggctt attgcatcac  10680
agtaattgct gtacgaaggt cagaatcgct acctattgtc caaagcagtc gtaagaagag  10740
gtcccaatcc cccactcttt ccgcccctaat ggaggtctcc agtttcggta aatataagta  10800
ataaggattg ttgggggggt ggagggaaat aattatttcc agcatgcgtt gcggaatgaa  10860
aggtcttcgc cacagtgttc cttagaaact gtagtcttat ggagaggaac atccaatacc  10920
agagcgggca caattctcac ggaaatccag tggatagatt ggagacctgt gcgcgcttgt  10980
acttgtcaac agttatggac tggagtgtta tgttttcgta ttttgaaagc agaaactagg  11040
ccttaaaaag atacgtacaa ctctttaggg agactacaat tcccatccag ccccaggagt  11100
ctggggcaag tagtcttgta aggtcagtgg cctgcgggga cgcagtgagc gccgaatttg  11160
cctggggcag gggaaatgcg ctctggccca tgtctgcgca ctcgtagttc cacccctcag  11220
ccccagtgtt tgttatttt cgggttcagc ttgcttttgc cccgtctccg tcgacgcaat   11280
cgccaccagt caatggggtg gtcgttttga gggacaagtg gtaagagcca atcttcttgg  11340
cgaaaacgcg gagaaacggg actagttact gtctttgtcc gccatgttag attcaccca    11400 cagagatagc ggcagagctg gcagcggacg tctttgcat tgccgcctcc ccaggggggg    11460
ggaagctggt aaggaagcag cctggggttag ctagggtgg ggtcacgtca cactaagagg  11520
gtttggagaa gttcaaggga ggaatcctgc aaagaagagg ggcgactttt tccgtgtctc  11580
```

```
cggacagcta atcgttttag tgacaggatg agagagccct tcgtgttctg agggaccgag    11640
tgggcgaaaa gcgccggaga gttggagagt ctgtggttca gaatgcgagg tgacaacgtg    11700
ctagcagccc tcgctcgctc tcggcgcctc ctcggccttg gcgtccattc tggccgtgct    11760
ggaggagccc ttcagcccgc cactgcgctg tgggggcccc tctctgggct ggccgaagcc    11820
agagccggct ccctctgctt gcggggaagt gtggagggag aggcgggtgt gggaactggg    11880
gctgcgcgca gcgctcgcca gccagcgcga gttccaggtg ggcgcgggct cagcgggccc    11940 cgcaccccg gccccgggca gtcaggggcc tagcacccgg gccagcagct gcagagggtg    12000
cgccgggtcc cccagcactg ccggcccgcc tgcaccccgc ttgaattctc accgggcccc    12060
agccgccctg cacagggcaa ggctcaggac ctgcagcccg ccatgcccga gcccctccc     12120 aaccctgtg agctccagcg tggcctgagc ctccccgacg ggcaccgccc cctgctcctc     12180
agcgcccggt cccatcgact gcccaagggc tgagaggagt gcaggcgccc ggcacagccc    12240
tgcgcaggat ccactaggtg aagccagctg ggctcctgag tcagatgggg acttggaaaa    12300
cttttatgtc tagcctgagg attttatatg caccagtcag cactctgtgt ctagcttggg    12360
gtttggggat gcaccaatca gcactctgta tctagctaat ctggtgggca cttggagaac    12420
ttctgtgtct agctaaagga ttgtaaatgc accaatcagt gctctgtgtc tagctcaagg    12480
tttgcaaatg caccaatcag cactctgtgt ctagctaaag gtttgtaaac gcaccaatca    12540
gtgctctgtg tctagcaaat gtagtgggga cttgagaat tttatgtct agctagagga      12600 ttgtaaatgc accatcagc actctgtgta tatctagctc agggattgta atgcaccaa      12660 tcagcacccct gtcaaaacgg accaattagc tctctgtaaa atggaccaat caacaggatg   12720
tgggtggggt cagataaggg aataaaagca ggctgccccg ctgggtgcca gtggctcaca    12780
cctgtaatcc cagcaatttg ggaggcctag aggggtggat cacgaggtca agagatcgag    12840
accatcctgg ctaacacagt gaaaccccga ctctactaaa aagacaaaat attagctggg    12900
tgcggtggtg ggtgcctgta atcccctcta ctggggaggt tgaggcagga gaatggcgtg    12960
aacccgggag gcggagcttg cagtgagccc agattgcacc actgcattcc agcctgggtg    13020
acagagggag actccatctc aaaaaaaaaa aaaaaaaaa aaaaaaatgc aggctgcctg     13080
agccagcagc agcaacccgc tctggtctcc ttccacgctg tggaagcttt gttcttgtgc    13140
tctttgcaat aaatcttgct gctgctcact ctttgggtcc gcatagcatt tatctgctgg    13200
taacaccgac cgcagaggtc tgcagcttca ctcctgaagc cagcgagacc acgaacccac    13260
caggaggaat gaacaactcc agacgggagg aacgaacaaa ctccagacat gccgccttaa    13320
gagctgtaac actcaccgca aaggtctgca gcttcactcc tgaagccagc gagaccacga    13380
atccaccaga aggaggtaac tctgaacacg tccgaacatc agaaggaaca aactctggac    13440
acatcatctt taagaactgt accactcacc gtgagggtcc gcaacttcat tcttgaagtc    13500
agtgagacca agaacccacc aatttcggac acaagaacat ccggcttcta ctgatggaag    13560
gccacgactc ctcagtagaa agagggccca ggcaaagaaa atgagagaga gtccttgggg    13620
tggtgacact atcttgggaa catggagtgc taggaaacga taactggaag actaggatga    13680
aatctgcaag ttaaaaaatg acactaccca tatatccttc tcatcccatt ctccttttt     13740 cgagacccg ttaaagagat cttggttagg gaccttttggt tttggaaagg cactgtttct    13800
cctttttgtc aaacactcaa ctttcaggcc acacttttt tttttttttc gagacaaagt     13860
ctcgctttct caaagaccag cccaggctgg tcttgaactc ctgagctcaa gcgatcctcc    13920
tgccttggcc tcccaaagtg ctgggattac aggcatgagc caccactccc ggcctcagct    13980
```

```
tggataactt ggcttgtaca ggcctctggt ggagacagta accaaagttc gggttgccag   14040
gtttgtttca ttaagggat tttgttgagg ctgaaagaaa aaaaaatcga tgtggaggaa    14100
aagctaactt gtgccaagac aaggtgagtc agtcacatgg acttaacaat aatgtcaatt   14160
atgaaagctg aaggcctagg acccagctat ctgactctac tggctgtaga cctaaggagc   14220
aggtagggtt aaccatagct ttcgtgttta cacacgttca agattaatgc tcttgctgaa   14280
agaatttttt tacatgccag ccaaagagag ttccttatgg agacctggat atggtccagc   14340
taagctagaa tctcccactt cctgttttct cttagttggc ccaccagctg gaggagctcc   14400
agaatatcta aattaatttc caattgtgta atttgagaaa aagagacgaa gattaatttc   14460
cctaacgagt agggaagtgt gtttcttttt tttcttttt ttttgagact gagtctcgct    14520
ctgtcgccca gcctgaagtg cagtggcacg atcgcggcta gtgcactgcg aactctgtct   14580
cccgggttca cgccattctc ctgcctcagc ctcccgagta gctgggacta caggcacccg   14640
ccatcacgcc cagctaattt tttgtgtttt tagtagagat ggggggtttca ccgcgttagc   14700 caggatgacc tcgatctcct gacctcgtga tctgccttcc tcggcctccc aaagtgctgg   14760
gattataggc gtgagccacc gcacctggca ggaagtgttt cttaaagttg gaaagtggta   14820
tttcagaata tccgcttttg gcagactgag tcagtcactt cattttcctg attttttgcc   14880
taaggtcctg gtgaattgac aaagattctg cccaaatttt aacgacccca gtaattacat   14940
gtcatatgaa tgaatacttg acgtcagcag gactgcgttt tggtggtgaa cttggttcta   15000
ggtagaaaca aagaatggag aaaactgggg gataattatc ttagggtttc aaaaaagtgc   15060
ctgatcttca cagacttcag ggtccttaaa ataacagtct taattgtagt gttttacagg   15120
gcagtgcatt acattgtcaa aaacagtaca ggtttatggt tctaatgact ggtttattat   15180
ttttaaaaat gtttaattga acttaatttt ttaaggaga cagggtccgg ctttgttgcc    15240
caggctggtc ttcaactcct aggttcacga tccttccacc tcagcctccc aaattgctag   15300
gattacaggc atgagccacc acccgggcc aatttttat tttattttg agacagagtc     15360 tcgctctatc acccaggcgg gagtgcagtg gcatgatctt ggcgcactgc aaccttgcct   15420
cccagattca agcaattctc ttgcctcagc ctcttgagta gctgggaata caggcctgcg   15480
ccactacacc cagctaattt ttgtattttt attagagacg aagtttcacc atgttggcta   15540
ggctggtctc gaactcctgg actcaagcga tctgcctgcc tctgcttccc aaaatcctgg   15600
gattacagac atgagccact gtgcctggcc tgtattataa tattttata tttgaatgac   15660 attttgaaag aacttgcata ttcattttta atttgatcct tatggtaaca ctgtgagatc   15720
ggcaaaacag acatattaga cctattttac agattaaaga actgaagctc aaaggtgaac   15780
tgacctgctc acagttttat gtctagtaat gggccagagc tgtgtctaga cccaagtct    15840 tcccattttt tgtgctcaca cacatacaca caatttgctg ttctgattag atgacatttc   15900
attgctttca atttgcattg ttctgaccac cagaaagttt gaaagtcttc tgaggtattt   15960
gttaggtgtt ctgacttctt ctatgaattt tatgtatact ttttcctggg ttgttaattg   16020
tatcattagc agttttgctg atactctggg tgtgttgcag atattaaccc tttgctgtgg   16080
gttgtgatgg ttgtttgttg tcttctgatt ttgtggattt ttttaaccat ataaaatatt   16140
tagtatgtaa tgaaatatgc ccaactcatc ctttgacttc tatgtacatt ataacctgcc   16200
tttaaatgtg tatttctttt gtaggtaaaa gtttcatttg atctgaatag tattaaaata   16260 aaataccctgg atgaggaaga tgaagaggta aagtatatta tggtacttat tgctaggtgt  16320
```

```
tcagaatagg gatcttattt ctccagtgat atgggcttta ataattcgaa gtagcgctta  16380
gctcatttgt gtctcaaaat aataataata ataataaaaa caatgagaca tgcaagagat  16440
gtcgggagaa gcaccagaag attccattga aatcttgctc cccagaaggg tgggaacagt  16500
agggacagaa aactgctgtg gttcattatg tttcatcccc atttcgcttc attttattga  16560
accccgtctc tactaaaaat acaaaaaatt agccaaatgt ggcagcaggc gcctgtagtc  16620
ctagctactt gggaggctga ggcaggagaa tggcgtgaac ccaggaggcg gagcttgcag  16680
tgagccgaga tcgtgccact gcacttcagc ctcggtgaca gagcgagact ccgtctcaaa  16740
aaaaaaaaaa ggatatcagc ttttttatttt cttttctttt ctcctttttct ttctttgctt  16800 tgcttttctt tttgttttgg gacagagtct cactctgtca tccaggctgc agtgcagtgg  16860
cgcaatctca gctcactgca acctctgctt cctgggttga agcgattctt gtgcctcagc  16920
ctcccaagta gctgggacta caggcatgca ccaccatgcc tggctaattt ttgtatattt  16980
ggtagaaatg gggtttcacc atgttggcca ggctggtttt gaactcctgg cctcaagcaa  17040
tccagcggcc tcagcctccc aaagttatgg gattacaggc atgagccatt gtgcccagcc  17100
aggatatcat catatttaat cctcacatca actgacattt gccccaattt acagatgagg  17160
aactgaggca cagagaggtt ttggtacttg cctgaggtca cacactctgg gctctctgct  17220
tggggctgag ggccaagggg ggttgtgact gacttctctt tcctgaacat caataaaatt  17280
caatttagaa atttctgtct tcagtgctat ctcgagggggc ctgtgaaaaa tgctgactcg  17340
gtggcagctg tcttagcccc atactcattg ggttgccctg agcccacac tgttttaagg  17400 aagtcccagc aaataatatg ggatagaggt gagatccaaa cctaagcagc cctggctcta  17460
aaacccactg aacaaagctg cctctccaac tagcatcaga aagaactagg tgagaatcct  17520
acttctatca cttactagtt ctgtggctct ggccgcccccc gcccaagtta cttaacctct  17580 ttttttttt ttcctttttc ttttttctttt tttagagacg aagtctcgct ctgtcaccag  17640
gctggagtgc agtggcgtga tcttggctca ctgcaacctc tgcctccggg ttcaagcaat  17700
tctcctgctt cagcctcccg agtagcttgg gactacagac gtgcgcaacc atgcccagct  17760
aattcttttt ttcttttattt tatttttattt ttttttttga gatggagtct cgctctgtcg  17820
cccaggctgg agtgtagtgg cgcgatcttg gctcactgca agctctgcct cccgggttca  17880
cgccattctc ctgcctcagc ttcctgagta gcttggacta caggcgccca ccagcacgcc  17940
cagctaattt tttttttttct ttgtattttt agtagagacg gggtttcact gtgttagcca  18000
```

METHODS FOR THE DETECTION OF SEQUENCE AMPLIFICATION IN THE BRCA1 LOCUS

CROSS-REFERENCE TO RELATED APPLICATIONS (none)

STATEMENT REGARDING FEDERALLY SPONSORED RESEARCH OR DEVELOPMENT (none)

REFERENCE TO MATERIAL ON COMPACT DISK (none)

BACKGROUND OF THE INVENTION

Field of the Invention

The invention relates to a method for detecting the amplifications of sequences in the BRCA1 locus, which sequences have ends consisting of or are framed with sequence stretches present at least twice in the BRCA1 locus, and which amplification results in at least two or at least three, especially three, tandem copies of the amplified sequence. This invention also relates to methods for determining a predisposition to diseases or disorders associated with these amplifications, including predisposition to ovarian cancer or breast cancer. This invention also relates to a method for detecting amplifications with similar features in other loci.

Description of the Related Art

Breast cancer is the most common malignancy in women, affecting approximately 10% of the female population. Incidence rates are increasing annually and it is estimated that about 1.4 million women will be diagnosed with breast cancer annually worldwide and about 460,000 will die from the disease. Germline mutations in the hereditary breast and ovarian cancer susceptibility genes BRCA1 (MIM#113705) and BRCA2 (MIM#600185) are highly penetrant (King et al., 2003), (Nathanson et al., 2001). BRCA1 and BRCA2 genes, together with other genes such as NBR2 gene have been identified, characterized and mapped in the human genome and these data are publicly available. Screening is important for genetic counseling of individuals with a positive family history and for early diagnosis or prevention in mutation carriers. When a BRCA1 or BRCA2 mutation is identified, predictive testing is offered to all family members older than 18 years. If a woman tests negative, her risk becomes again the risk of the general population. If she tests positive, a personalized surveillance protocol is proposed: it includes mammographic screening from an early age, and possibly prophylactic surgery. Chemoprevention of breast cancer with anti-estrogens is also currently tested in clinical trial and may be prescribed in the future.

Most deleterious mutations consist of either small frameshifts (insertions or deletions) or point mutations that give rise to premature stop codons, missense mutations in conserved domains, or splice-site mutations resulting in aberrant transcript processing (Szabo et al., 2000). However, mutations also include more complex rearrangements, including deletions and duplications of large genomic regions that escape detection by traditional PCR-based mutation screening combined with DNA sequencing (Mazoyer, 2005). Only one amplification involving more than two copies has been reported so far (Hogevorst et al., 2003). This amplification is a triplication in the 3' portion of the BRCA1 gene, involving exons 17-19 and caused by Alu recombination.

Techniques capable of detecting these complex rearrangements include Southern blot analysis combined with long-range PCR or the protein truncation test (PTT), quantitative multiplex PCR of short fluorescent fragments (QMPSF) (Hofmann et al., 2002), real-time PCR, fluorescent DNA microarray assays, multiplex ligation-dependent probe amplification (MLPA)(Casilli et al., 2002), (Hofmann et al., 2002) and high-resolution oligonucleotide array comparative genomic hybridization (aCGH) (Rouleau et al., 2007), (Staaf et al., 2008). New approaches that provide both prescreening and quantitative information, such as qPCR-HRM and EMMA, have recently been developed and genomic capture combined with massively parallel sequencing has been proposed for simultaneous detection of small mutations and large rearrangements affecting 21 genes involved in breast and ovarian cancer (Walsh et al., 2010). Other techniques described for the detection of these complex gene rearrangements include Molecular Combing (Herrick and Bensimon, 2009); (Schurra and Bensimon, 2009); (Gad et al., 2001), (Gad et al., 2002a), (Gad et al., 2003); (Cheeseman et al. 2012); (U.S. 61/553,906).

Prior art methods are unable to detect and/or characterize amplifications when such amplifications involve more than one additional copy of the amplified sequence and/or when the amplified sequence includes portions of sequence present in multiple copies in the wild-type BRCA1 gene or surrounding locus and/or when the amplified sequence belongs to a portion of the BRCA1 locus with very high repeat content. Here, the inventors provide methods to detect and/or characterize such amplifications and to detect and/or characterize amplifications sharing similar features in other genomic loci.

BRIEF SUMMARY OF THE INVENTION

The BRCA1 and BRCA2 genes are involved, with high penetrance, in breast and ovarian cancer susceptibility. About 2% to 4% of breast cancer patients with a positive family history who are negative for BRCA1 and BRCA2 point mutations can be expected to carry large genomic alterations (in particular deletion or duplication) in one of the two genes, and especially BRCA1. However, some large rearrangements are missed by available techniques. This includes tandem amplification of sequences, characterized by the fact that more than one extra copy of the amplified sequence is introduced and/or characterized by the fact that the extremities of the amplified sequence (the sequence unit which undergoes repetition) are present in multiple copies—either perfectly or strongly homologous to each other—in the wild type locus, and/or when the amplified sequence is in a repeat-rich region.

Methods in vitro for detecting and/or characterizing these types of amplifications are one object of the invention. These include in vitro methods for detecting the triplication of a sequence fragment encompassing exons 1a, 1b and 2 of BRCA1 and fractions of the NBR2 gene. This region is particularly rich in Alu sequences and common copy number assessing techniques are unable to correctly characterize this triplication. The breakpoints of this tandem triplication share perfect sequence identity over 48 base pairs. This 48 base pair (bp) sequence is found in both BRCA1 and NBR2 genes in the reference human genome sequence.

The invention relates to tests or methods for this triplication and related amplifications, using Molecular Combing. This direct visualization approach allows immediate detection and characterization of these amplifications, and is not hindered by their repeat sequence content, homologous extremities or the number of copies. The invention also concerns tests or methods, which allow in vitro detection and characterization of this triplication and related amplification which are based on enrichment of a biological sample in specific DNA polynucleotides comprising the triplication. These methods are based on polymerase chain reaction (PCR), sequencing and other related techniques. Kits for performing such methods are also within the invention. The methods and kits bring substantial improvement over existing methods which are unable to detect such amplifications.

Results for four unrelated patients are disclosed, showing the triplication in all four patients' samples. The patients were also tested using other techniques of the prior art and the triplication could not be correctly detected or characterized, showing the substantial improvement the inventors brought to existing techniques.

The invention also concerns methods for determining predisposition (also designated as higher risk with respect to a population of reference) to ovarian or breast cancer based on these tests or methods. Furthermore, the inventors describe methods for adapting medical follow-up and/or treatment of patients with increased risk of breast or ovarian cancer and/or patients with ovarian breast cancer linked to this family of amplifications.

DETAILED DESCRIPTION OF THE INVENTION

Figure 1:
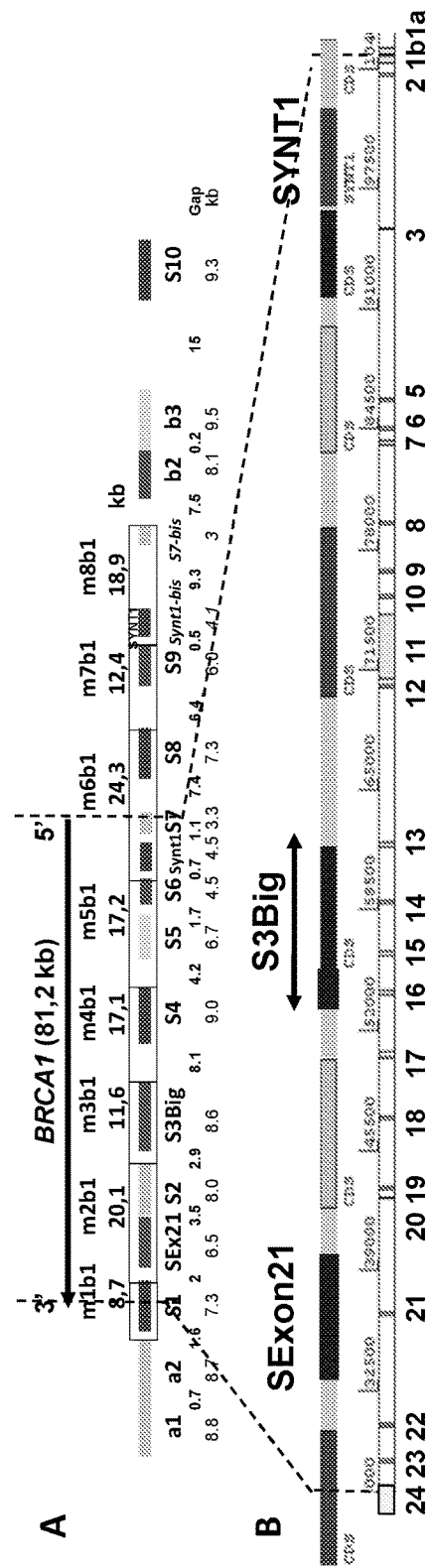
FIG. 1: In silico-generated Genomic Morse Codes 4.0 (GMC 4.0) designed for high-resolution physical mapping of the BRCA1 genomic region. (A) The complete BRCA1 GMC 4.0 covers a genomic region of 200 kb and is composed of 14 signals (a1/a2, S1, Sex21, S2, S3Big, S4, S5, S6, Synt1, S7, S8, S9, b2/b3, S10) of a distinct color (not illustrated). Each signal is composed of 1 to 2 small horizontal bars, each bar corresponding to a single DNA probe. The region encoding the BRCA1 (81.2 kb) and NBR2 (19.5 kb) genes is composed of 8 "motifs" (m1b1-m8b1), Each motif is composed of 1 to 3 small horizontal bars and a black "gap" (no signal). (B) Zoom-in on the BRCA1 gene-specific signals and relative positions of the 24 exons.

The invention disclosed herein provides methods for testing in vitro the presence of an amplification of a genetic sequence (e.g. stretch of DNA) in a biological sample containing nucleic acid representative of chromosomes, in particular nucleic acid representative of human chromosome 17, and in particular genomic nucleic acid of chromosome 17 comprising:
submitting said biological sample to a procedure allowing physical mapping of the region extending from exon 2 of the BRCA1 gene to the NBR2 gene;
detecting more than two successive examples (copies) (duplication or more, in particular triplication) of a 6 kb- to 8 kb-sequence extending from intron 2 of BRCA1 to the NBR2 gene.

The invention also provides kits for testing in vitro the presence of an amplification of a genetic sequence in a sample using the method described herein.

The term "nucleic acid" and in particular "nucleic acid representative of chromosomes" as used herein designates one or several molecules of any type of nucleic acid capable of being attached to and stretched on a support as defined herein, and more particularly stretched by using molecular combing technology. Nucleic acid, and in particular "nucleic acid representative of chromosomes" also designates one or several molecules of any type of nucleic acid capable of being amplified using PCR or PCR-related methods or capable of being sequenced using sequencing methods. Nucleic acid molecules include DNA (in particular genomic DNA, especially chromosomal DNA, or cDNA) and RNA (in particular mRNA). A nucleic acid molecule can be single-stranded or double-stranded but is preferably double stranded.

"Nucleic acid representative of a given chromosome" means that said nucleic acid contains the totality of the genetic information or the essential information with respect to the purpose of the invention, which is present on said chromosome. In particular, it is chromosomal DNA.

Physical mapping, as used herein, is the creation, employing molecular biology techniques, of a genetic map defining the relative position of particular elements such as specified sequence stretches, mutations or markers on genomic DNA. Physical mapping does not require previous sequencing of the analyzed genomic DNA. A physical map obtained by a physical mapping method may include information on the distances or approximate distances separating particular elements or may be limited to information regarding the succession of these elements, i.e. the order in which they appear in the genomic region of interest.

In particular embodiments, the method of the invention involves using FISH or Molecular Combing or related direct mapping methods to allow physical mapping of the region extending from intron 2 of BRCA1 to the NBR2 gene.

FISH: Fluorescent in situ hybridization.

Molecular Combing is a technique for direct visualization of single DNA molecules that are attached, uniformly and irreversibly, to specially treated glass surfaces. Prior to nucleic acid stretching, nucleic acid manipulation generally causes the strand(s) of nucleic acid to break in random locations. Molecular Combing has been described in WO 95/22056, WO 95/21939, WO 2008/028931 and in U.S. Pat. No. 6,303,296.

Molecular Combing and related direct mapping methods or Molecular Combing or related direct mapping methods, as used herein, designates methods, including Molecular Combing, functionally similar to Molecular Combing, in that they provide means to directly measure distances or approximate distances separating given sequences on single DNA fibers. For some methods, precise determination of the distance between specified sequences is possible. Precise measurement may be understood to provide a distance accurate to 10,000 bp (10 kb), 1,000 bp (1 kb), 100 bp, 10 bp or 1 bp. For other methods, only approximate distance measurements are possible. For other methods yet, only a succession of sequences on a DNA fiber may be determined, i.e. the order in which these sequences are arranged on the DNA fiber, such sequences being possibly present several times on the DNA fiber. While these methods may not always provide means to measure accurately the size of an amplified sequence as addressed herein, they can nevertheless usually detect such amplifications when designed following the method disclosed by the inventors. Molecular Combing and related direct mapping methods may rely on direct measurement of the physical distance between the specified sequences, or on measurement of a physical value directly related to the physical distance between the specified sequences. Such physical values include time, if e.g. the DNA fiber is made to move at a known speed through a detector recording the time of passage of the specified sequences. Such values also include total fluorescence intensity passing through a detector, when such total fluorescence intensity may be related to total nucleic acid content and the DNA fiber is made to move in a detector that can record fluorescence intensity comprised through specified sequences. Such methods may also provide the means for direct reading of the succession of sequences of interest, if e.g. the sequences of interest are labeled with distinct markers or distinct combinations of markers, fluorescent or otherwise, and the method provides means for reading the succession of markers, i.e. the order in which the markers are arranged on the DNA fiber.

In certain embodiments, Molecular Combing and related direct mapping methods are DNA stretching methods. The nucleic acid sample is generally stretched on a support in linear and parallel strands using a controlled stretching factor. By stretching factor it is meant herein the conversion factor allowing to connect physical distances measured on the stretched nucleic acid to the sequence length of said nucleic acid. Such a factor may be expressed as X kb/μm, for example 2 kb/μm. By controlled stretching factor it is meant herein a technique for which the stretching factor is sufficiently constant and uniform to allow reliable deduction of the sequence length of a hybridization signal from the measured physical length, with or without the use of calibration probes on the tested sample.

Other DNA stretching methods may be used as an alternative to Molecular Combing. These methods include, for example:

methods based on the extraction of DNA with detergent and/or high salt concentration, combined or not with the incubation with an intercalating agent and/or UV-light, derived from the methods termed ECF-FISH (extended chromatin fibers-fluorescent in situ hybridization), Halo preparation, and other methods described in (Heng et al., 1992; Haaf and Ward, 1994; Wiegant et al., 1992; Florijn et al., 1995; Vandraager et al., 1998, Raap, 1998, Palotie et al., 1996; Fransz et al., 1996); and methods based on the stretching of DNA through the action of a hydrodynamic flow or through mechanical traction on the DNA molecules, by capillarity, gravity or mechanical force, possibly in a micrometer- or nanometerscale device, the DNA being or not immobilized on a solid support, derived from methods termed DIRVISH (direct visual hybridization), optical mapping, and other methods described in Parra and Windle, 1993; Raap, 1998; Heiskanen et al., 1994; Heiskanen et al., 1995; Heiskanen et al., 1996, Mann et al., 1996, Schwartz et al., 1993; Samad et al., 1995, Jing et al., 1998; Dimalanta et al., Palotie et al., 1996; Larson et al., 2006)

In particular embodiments, the method of detection of the invention comprising steps enabling Molecular Combing or related direct mapping method also comprises a hybridization step of nucleic acid representative of chromosome 17, with at least one probe or set of 2 probes or more allowing the identification of the region extending from intron 2 of BRCA1 to the 5' region of NBR2. Hybridization with said probe(s) enables determination of presence of repetition in particular duplication or triplication of amplified sequence of the invention.

In a particular embodiment, the hybridization step is followed by an analysis of the resulting hybridization pattern, consisting of or comprising:

comparing the resulting hybridization pattern with the theoretical hybridization pattern i.e., the hybridization pattern expected for a wild-type sample;

in cases where said resulting hybridization pattern contains additional signals when compared to said theoretical hybridization pattern, concluding that the sample contains a sequence amplification;

optionally, if the probes generating the additional signals cannot be unambiguously identified, performing additional hybridization steps with modified sets of probes allowing the unambiguous identification of the probes generating the additional signals;

optionally, if said additional signals consist of or comprise several identical patterns, concluding that the sequence amplification resulted in more than one additional copy of the amplified signal.

In particular embodiments, the Molecular Combing or related direct mapping method comprises a hybridization step of nucleic acid representative of chromosome 17, with at least the following probes:

one probe or set of probes allowing the identification of the intron 2 of the BRCA gene;

and one probe or set of probes allowing the identification of the 5' region of the NBR2 gene;

and optionally other probes to confirm the location and/or identify unambiguously the probes or sets of probes above.

As defined herein, a "probe" is a polynucleotide, a nucleic acid/polypeptide hybrid, a nucleic acid/polypeptide hybrid or a polypeptide, which has the capacity to hybridize to nucleic acid representative of chromosomes as defined herein, in particular to RNA and DNA by base pairing with said nucleic acid representative of chromosomes which is thus the target for the probe. In a particular embodiment, the probe is substantially or fully complementary to the target nucleic acid and accordingly enables stable hybrids to be formed in stringent conditions of hybridization and detected. This term encompasses RNA (in particular mRNA) and DNA (in particular cDNA or genomic DNA) molecules as well as, peptide nuclear acid (PNA), and protein domains. Said polynucleotide or nucleic acid hybrid generally comprises or consists of at least 100, 300, 500 nucleotides, preferably at least 700, 800 or 900 nucleotides, and more preferably at least 1, 2, 3, 4 or 5 kb. For example probes of 1, 2, 3, 4, 5, 6, 7, 8, 9, 10, 11, 12, 13, 14, 15 kb or more than 15 kb, in particular 30, 50 or 100 kb can be used. In a particular embodiment, the length of the probes used is ranging from 0.5 to 50 kb, preferably from 1 to 30 kb and more preferably from 1 to 10 kb, from 4 to 20 kb, from 4 to 10 kb, or from 5 to 10 kb. Said polypeptide generally specifically binds to a sequence of at least 6 nucleotides, and more preferably at least 10, 15, 20 nucleotides. As used herein, the sequence of a probe, when the probe is a polypeptide, should be understood as the sequence to which said polypeptide specifically binds. A probe specific for a given region of the genome or specific for a given sequence, as used herein, is a probe capable in certain conditions of hybridizing on said given region of the genome or on said given sequence while in the same conditions it does not hybridize to most other regions of the genome or to sequences significantly different from said sequence.

In a particular embodiment, the sequence of a probe is at least 99% complementary, i.e., at least 99% identical, or at least 99% similar to the sequence of a portion of one strand of the target nucleic acid to which it must hybridize.

The term "complementary sequences" in the context of the invention means "complementary" and "reverse" or "inverse" sequences, i.e. the sequence of a DNA strand that would bind by Watson-Crick interaction to a DNA strand with the said sequence.

Generally, a probe will be tagged or labeled with a marker, such as a chemical or radioactive market that permits it to be detected once bound to its complement. The probes described herein are generally tagged with a visual marker, such as a fluorescent dye having a particular color such as blue, green or red dyes. Some probes according to the invention are selected to recognize particular portions or segments of the BRCA1 gene and surrounding locus.

In a particular embodiment, the nucleic acid sample used for Molecular Combing or related direct mapping methods is genomic DNA, in particular total genomic DNA or more preferably chromosomal genomic DNA (nuclear genomic DNA), and/or fragments thereof. Said fragments can be of any size, the longest molecules reaching several megabases (thousands of kb). Said fragment are generally comprised between 10 and 2000 kb, more preferably between 200 and 700 kb and are in average of about 300 kb.

The nucleic acid sample used in the method of the invention can be obtained from a biological fluid or from a tissue of biological origin, said biological sample, including tissue, being isolated for example from a human (also called patient herein).

Sequence lengths are expressed herein in kb (kilo base pairs, i.e. 1000 base pairs) or by (base pairs). The length of genetic sequences is usually measured on double stranded nucleic acid and thus expressed in base pairs, where every base pair is made of one nucleotide on one strand and its complementary nucleotide on the other strand. If applied to a single-stranded nucleic acid, the measurement in base pairs is understood to correspond to the measurement of the corresponding double-stranded nucleic acid, i.e. the nucleic acid made of the single-stranded nucleic acid of interest paired with its reverse complementary nucleic acid.

In a particular embodiment, the invention consists of or comprises:

hybridizing a nucleic acid representative of chromosome 17 with a set of probes including at least one probe or set of probes allowing to identify the region extending from intron 2 of BRCA1 to the NBR2 gene or a portion of this region;

measuring the size of the region recognized by said probe or set of probes;

comparing the measured size with the size of a single copy of said region or said portion of said region, in the case where the measured size is greater than the size of a single copy of said region or said portion of said region, concluding that the sample contains a sequence amplification in said region;

and, optionally, if the measured size is greater than the expected size of two tandem copies of said region or said portion of said region, concluding that the sample contains a sequence amplification in said region, with more than one additional copy of the amplified sequence.

In a particular embodiment, the hybridization step is followed by an analysis step consisting of or comprising:

determining the location of the breakpoint on one end of the amplified sequence and/or a confidence interval for the location of said breakpoint;

determining the size of the amplified sequence and/or a confidence interval for the size of the amplified sequence;

determining from the above location and size and/or confidence intervals for the location and/or size the location and/or a confidence interval for the location of the breakpoint at the other end of the amplified sequence.

The invention disclosed herein also provides methods for testing in vitro the presence of an amplification of a genetic sequence in a patient's genome, such method comprising:

obtaining a DNA sample from the patient;

submitting the DNA sample to a procedure allowing physical mapping of the genomic region extending from intron 2 of the BRCA1 gene to the NBR2 gene;

detecting more than two successive copies of a 6 kb- to 8 kb-sequence extending from intron 2 of BRCA1 to the NBR2 gene.

The invention also provides kits for testing in vitro the presence of an amplification of a genetic sequence in a patient's genome using the method described in the previous paragraph.

Wild-type: this expression designates an unmodified sequence for a given gene or genomic region, i.e. the gene or genomic region bearing the sequence published in the reference human genome sequence. Since only large rearrangements are considered herein, where more than 1 kb of sequence have been modified (deleted, amplified, inverted or modified otherwise) relative to the reference sequence, the expression wild-type designates a sequence with less than 1 kb differing from the reference human genome sequence.

PCR: polymerase chain reaction

PCR and related methods: as used herein, this expression designates any method allowing the detection in a sample and optionally the quantification of one or several fragments of DNA characterized by the sequences of their extremities and itheir sizes. This includes but is not restricted to PCR, quantitative PCR, isothermal amplification (Gill and, Ghaemi, 2008), multiplex, ligation-dependent probe amplification (MLPA, Schouten et al., 2002)

Breakpoint: as used herein, this expression designates the position in the genome of the extremities of a rearrangement found in a DNA sample. This implies that on one side of a breakpoint, the sequence of the DNA sample is identical to the reference human genome sequence, while on the other side the sequence differs from the wild-type sequence. A sequence overlapping the breakpoint would also differ from the reference human genome sequence.

Reference human genome sequence: the reference sequence used herein is the human genome Build GRCh37/hg19. The sequence corresponding to positions 41,267,001 to 41,285,000 of the human reference genome sequence build GRCh37/hg19 of human chromosome 17 is provided as SEQ ID No. 22.

genomic position: genomic positions are given as nucleotide positions corresponding to the reference human genome numbering. Genomic coordinates is used herein with the same meaning. Unless otherwise specified, genomic coordinates or positions given herein are from chromosome 17. A genomic position is described herein as "upstream" of another position on the same arm of a chromosome if it is located closer to the centromere (e.g. has a smaller position number if both are on the "q" arm of chromosome 17). Conversely, a genomic position is described as "downstream" of another position on the same arm of a chromosome if it is located further from the centromere (e.g. has a larger position number if both are on the "q" arm of chromosome 17).

Adaptation of medical follow-up: as used herein, this expression designates the modification of medical or clinical surveillance for a patient when e.g. the risk of cancer in this patient or predisposition is increased relatively to the general population. For example, a periodic monitoring of biological or clinical characteristics may be advisable for the general population with a given frequency (e.g. in the case of breast cancer, mammographies may be recommended every 5 years), while this monitoring may be advisable with higher frequency for patients at elevated risk of a disease (e.g. in the case of an elevated risk or breast cancer, mammographies may be recommended every year). The adaptation of medical follow-up may be the prescription or recommendation of an adapted follow-up—whether the patient follows the prescription or recommendation or not —; the implementation of the adapted follow-up, or any other action performed aiming to adapt medical follow-up.

Predictive genetic testing: screening procedure involving direct analysis of DNA molecules isolated from human biological samples (e.g.: blood), used to detect gene mutations associated with disorders that appear after birth, often later in life. These tests can be helpful to people who have a family member with a genetic disorder, but who have no features of the disorder themselves at the time of testing. Predictive testing can identify mutations that increase a person's chances of developing disorders with a genetic basis, such as certain types of cancer.

Polynucleotides: This term encompasses naturally occurring DNA and RNA polynucleotide molecules (also designated as sequences) as well as DNA or RNA analogs with modified structure, for example, that increases their stability. Genomic DNA used for Molecular Combing will generally be in an unmodified form as isolated from a biological sample. Polynucleotides, generally DNA, used as primers may be unmodified or modified, but will be in a form suitable for use in amplifying DNA. Similarly, polynucleotides used as probes may be unmodified or modified polynucleotides capable of binding to a complementary target sequence. This term encompasses polynucleotides that are fragments of other polynucleotides such as fragments having 5, 10, 15, 20, 30, 40, 50, 75, 100, 200 or more contiguous nucleotides.

BRCA1 locus: This locus encompasses the coding portion of the human BRCA1 gene (gene ID: 672, Reference Sequence NM_007294) located on the long (q) arm of chromosome 17 at band 21, from base pair 41,196,311 to base pair 41,277,499, with a size of 81 kb (reference genome Build GRCh37/hg19), as well as its introns and flanking sequences. Following flanking sequences have been included in the BRCA1 GMC: the 102 kb upstream of the BRCA1 gene (from 41,277,500 to 41,379,500) and the 24 kb downstream of the BRCA1 gene (from 41,196,310 to 41,172,310). Thus the BRCA1 GMC covers a genomic region of 207 kb.

BRCA1 gene and surrounding locus: this expression designates herein the human genome portion containing the BRCA1 gene and ~300 kb flanking portions on either side and corresponds to genomic positions 40,900,000 to 41,600,000.

Intron 2 of BRCA1: as used herein, this expression designates the genome region comprised between exon 2 and exon 3 of BRCA1, or between genomic positions 41,267,770 and 41,276,000.

NBR2 gene: this gene is mapped in the human genome reference sequence to positions 41,277,600-41,292,342. As used herein, the 5' region of NBR2 is the genomic region comprised between positions 41,277,600 and 41,282,600

A sequence extending from intron2 of BRCA1 to the NBR2 gene: this expression designates a sequence having one extremity in the intron 2 of BRCA1 and one extremity in the NBR2 gene. Such a sequence would necessarily include exons 1a, 1b and 2 of BRCA1. Such a sequence would have one extremity located upstream of genomic position 41,276,000 and one extremity located downstream of genomic position 41,277,600.

Region extending from intron2 of BRCA1 to the NBR2 gene: this expression designates the human genome portion extending from genomic positions 41,270,000 (a position located between exons 2 and 3 of BRCA1) to 41,282,600 (a position located in the NBR2 gene).

Germline rearrangements: genetic mutations involving gene rearrangements occurring in any biological cells that give rise to the gametes of an organism that reproduces sexually, to be distinguished from somatic rearrangements occurring in somatic cells.

Amplified sequence encompasses within the invention a stretch of DNA which undergoes repetition (i.e. is copied) in a genome and in particular is repeated so that at least two identical stretches of said DNA, or at least three identical stretches of DNA are present in the considered genome or genomic locus. In particular, the considered stretch of DNA is duplicated (1 additional copy of the stretch of DNA are present, i.e., a same sequence is present two times in the genome or genomic locus) or triplicated (2 additional copies of the stretch of DNA are present, i.e. a same sequence is present three times in the genome or genomic locus). Tandem amplification: mutations characterized by a stretch of DNA that is duplicated to produce two or more adjacent copies, resulting in a tandem repeat array.

Tandem repeat array: a stretch of DNA consisting of two or more adjacent copies of a sequence. A single copy of this sequence in the repeat array is called a repeat unit. Gene amplifications occurring naturally are usually not completely conservative, i.e. in particular the extremities of the repeated units may be rearranged, mutated and/or truncated. In the present invention, two or more adjacent sequences with more than 90% homology are considered a repeat array consisting of equivalent repeat unit. Unless otherwise specified, no assumptions are made on the orientation of the repeat units within a tandem repeat array. Such repeat units within a tandem repeat array may be separated by less than 100, or less than 10, or less than 5 or 0 nucleotides that do not belong to the repeated sequence.

Complex Rearrangements: any gene rearrangement that can be distinguished from a simple deletion or a simple duplication. Examples are translocations or inversions, or combinations of several duplications, or combinations of deletions and duplications.

Detectable label or marker: any molecule that can be attached to a polynucleotide and which position can be determined by means such as fluorescent microscopy, enzyme detection, radioactivity, etc, or described in the US application nr. US2010/0041036A1 published on 18 Feb. 2010.

Primer: This term has its conventional meaning as a nucleic acid molecule (also designated sequence) that serves as a starting point for polynucleotide synthesis. In particular, Primers may have 20 to 40 nucleotides in length and may comprise nucleotides which do not base pair with the target, providing sufficient nucleotides in their 3'-end, especially at least 20, hybridize with said target. The primers of the invention which are described herein are used in pairs in PCR procedures, or individually for sequencing procedures.

Genomic Morse Code(s): A GMC is a series of "dots" (DNA probes with specific sizes and colors) and "dashes" (uncolored spaces with specific sizes located between the DNA probes), designed to physically map a particular genomic region. The GMC of a specific gene or locus is characterized by a unique colored "signature" that can be distinguished from the signals derived by the GMCs of other genes or loci. The design of DNA probes for high resolution GMC requires specific bioinformatics analysis and the physical cloning of the genomic regions of interest in plasmid vectors. Low resolution CBC has been established without any bioinformatics analysis or cloning procedure.

Repetitive sequences: the BRCA1 and BRCA2 gene loci contain repetitive sequences of different types: SINE, LINE, LTR and Alu. Such repetitive sequences are known to make molecular testing difficult due e.g. to non-specific binding of primers. Such repetitive sequences, and regions rich in repetitive sequences, are known to be prone to rearrangements, potentially due to homologuous recombination or similar mechanisms (van Binsbergen et al. 2011).

The term "sample" or "biological sample" as used herein relates to a material or mixture of materials, typically, although not necessarily, in fluid form, containing one or more components of interest. For Molecular Combing, the sample will contain genomic DNA from a biological source, in particular suitable for for diagnostic applications, usually obtained from a patient. The invention concerns means, especially polynucleotides, and methods suitable for in vitro implementation on samples.

The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The term "stringent conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

A "stringent hybridization" and "stringent hybridization wash conditions" in the context of nucleic acid hybridization (e.g., as required for Molecular Combing or for identifying probes useful for GMC) are sequence dependent, and are different under different experimental parameters. Stringent hybridization conditions that can be used to identify nucleic acids within the scope of the invention can include for example hybridization in a buffer comprising 50% formamide, 5×SSC, and 1% SDS at 42° C., or hybridization in a buffer comprising 5.times.SSC and 1% SDS at 65° C., both with a wash of 0.2×SSC and 0.1% SDS at 65° C. Exemplary stringent hybridization conditions can also include a hybridization in a buffer of 40% formamide, 1M NaCl, and 1% SDS at 37° C., and a wash in 1×SSC at 45° C. Alternatively, hybridization to filter-bound DNA in 0.5 MNaHPO$_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1 M NaCl, 0.5% sodium sarcosine, 50 mM IVIES, pH 6.5. Those of ordinary skill will readily recognize that alternative but comparable hybridization and wash conditions can be utilized to provide conditions of similar stringency.

A probe or primer located in a given genomic locus means a probe or a primer which hybridizes to the sequence in this locus of the human genome. Generally, probes are double stranded and thus contain a strand that is identical to and another that is reverse complementary to the sequence of the given locus. A primer is single stranded and unless otherwise specified or indicated by the context, its sequence is identical to that of the given locus. When specified, the sequence may be reverse complementary to that of the given locus. In certain embodiments, the stringency of the wash conditions that set forth the conditions that determine whether a nucleic acid is specifically hybridized to a surface bound nucleic acid. Wash conditions used to identify nucleic acids may include for example a salt concentration of about 0.02 molar at pH 7 and a temperature of at least about 50° C. or about 55° C. to about 60° C.; or a salt concentration of about 0.15 M NaCl at 72° C. for about 15 minutes; or a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be for example 0.2×SSC/0.1% SDS at 42° C.

A specific example of stringent assay conditions is rotating hybridization at 65° C. in a salt based hybridization buffer with a total monovalent cation concentration of 1.5 M followed by washes of 0.5×SSC and 0.1×SSC at room temperature.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may be employed, as appropriate.

"Sensitivity" describes the ability of an assay to detect the nucleic acid of interest in a sample. For example, an assay has high sensitivity if it can detect a small concentration of the nucleic acid of interest in sample. Conversely, a given assay has low sensitivity if it only detects a large concentration of the nucleic acid of interest in sample. A given assay's sensitivity is dependent on a number of parameters, including specificity of the reagents employed (such as types of labels, types of binding molecules, etc.), assay conditions employed, detection protocols employed, and the like. In the context of Molecular Combing and GMC hybridization, sensitivity of a given assay may be dependent upon one or more of: the nature of the surface immobilized nucleic acids, the nature of the hybridization and wash conditions, the nature of the labeling system, the nature of the detection system, etc.

The invention thus relates to each and any of the following embodiments taken individually or in any combination. In particular, the invention concerns the following methods.

The invention relates to a method for in vitro detection of large rearrangement in the BRCA1 gene contained in nucleic acid of a biological sample comprising nucleic acid representative of chromosomal nucleic acid, in particular nucleic acid of human chromosome 17, comprising the step of detecting multiple copies of a target amplified sequence which is a sequence including exons 1a, 1b and 2 of the BRCA1 gene in the human 17 chromosome.

In a particular embodiment of the invention, the method for in vitro detection of large rearrangement in the BRCA1 gene contained in nucleic acid of a biological sample comprising nucleic acid representative of chromosomal nucleic acid, in particular nucleic acid of human chromosome 17, comprises the step of detecting multiple copies of a target amplified sequence which is a sequence having a size in a range of 6 kb to 8 kb and extending from intron 2 of the BRCA1 gene to the 5' end of the NBR2 gene in the human 17 chromosome.

According to another embodiment, a particular method for in vitro detection of large rearrangement in the BRCA1 gene according to the invention comprises steps of:
  providing the nucleic acid of the biological sample which comprises the target amplified sequence in conditions that enable hybridization with a probe or a set of probes, in particular providing the nucleic acid of the biological sample which comprises the target amplified sequence as isolated nucleic acid;
  contacting said provided nucleic acid with a probe or a set of probes in conditions enabling hybridization of the probe(s) with the target sequence, wherein each probe hybridizes with all or part of the amplified sequence extending from intron 2 of the BRCA1 gene to the 5' end of the NBR2 gene,
  detecting signals corresponding to hybridized probe(s), in particular by visualization. In a preferred embodiment of the method for in vitro detection of large rearrangement in the BRCA1 gene according to the invention, the detected amplified nucleic acid sequence is present in a copy number of at least 3 successive copies, in particular a copy number of 3 thereby characterizing a triplication in tandem of the target amplified sequence in the biological sample.

A method for in vitro detection of large rearrangement in the BRCA1 gene according to another particular embodiment of the invention, comprises a step wherein the detection of multiple copies of the target amplified sequences comprises measuring the size of the nucleic acid sequence hybridized to the probe(s) and comparing said measured size to the size of the amplified sequence taken as a single copy which is in a range of 6 kb to 8 kb.

In a further particular embodiment of a method for in vitro detection of large rearrangement in the BRCA1 gene according to the invention, the nucleic acid representative of chromosomal nucleic acid, in particular nucleic acid of human chromosome 17 is stretched prior to contacting with the probe(s).

The invention relates in a particular embodiment, to a method for in vitro detection of large rearrangement in the BRCA1 gene as defined herein, wherein the target sequence consists of the sequence extending from position 41,272,683 to position 41,279,942 in human chromosome 17 or a sequence framed by nucleic acid sequences consisting of the 48 base pairs sequence at position 41,272,683 in the BRCA1 gene and the identical sequence in the NBR2 gene.

A further particular embodiment of the method for in vitro detection of large rearrangement in the BRCA1 gene according to the invention is a method wherein the set of probes comprises or consists of a mixture of probes comprising Synt1 probe having a nucleic acid sequence base pairing with a genomic sequence starting with nucleotide at position 41,269,785 and ending with nucleotide at position 41,274,269 and S7 probe having a nucleic acid sequence base pairing with a genomic sequence starting with nucleotide at position 41,275,399 and ending with nucleotide at position 41,278,707, said probes being labeled with different markers or labels, in particular with a marker or label enabling visualization of a different color for each probe when detected.

A method for in vitro detection of large rearrangement in the BRCA1 gene according to a particular embodiment of the invention is a method wherein the Synt1 probe has the sequence amplified by primers Synt1F (SEQ ID No. 17) and Synt1R (SEQ ID No. 18) on a nucleic acid representative of the human BRCA1 gene or has the sequence of SEQ ID No. 1 and the S7 probe has the sequence amplified by primers S7F (SEQ ID No. 19) and S7R (SEQ ID No. 20) on a nucleic acid representative of the human BRCA1 and NBR2 genes or has the sequence of SEQ ID No. 2.

According to the definition of the invention provided herein, a particular method for in vitro detection of large rearrangement in the BRCA1 gene, comprises the steps of:
providing isolated nucleic acid representative of chromosomal nucleic acid that comprises the target amplified sequence, in particular isolated nucleic acid of human chromosome 17, in particular isolated genomic DNA of human chromosome 17 in a combing vessel;
performing molecular combing on said nucleic acid; to stretch the nucleic acid and provide physical mapping of said stretched nucleic acid;
contacting combed nucleic acid with a labeled probe or a set of probes wherein each of the probe hybridizes with a distinct region of the target amplified sequence and is labeled with a different label, in conditions enabling hybridization of the probes with the target amplified sequence;
washing the reaction mixture after hybridization;
detecting the signals corresponding to hybridized labeled probes.

According to a further embodiment, a method for in vitro detection of large rearrangement in the BRCA1 gene of the invention is a method wherein the detection of signals corresponding to hybridized labeled probes of a set of probes encompasses detecting hybridization patterns and determining the succession of hybridized probes, their identity and their length.

According to a further embodiment of the invention, the method for in vitro detection of large rearrangement in the BRCA1 gene, further comprises a step of comparing the detecting hybridization patterns reflecting the succession of hybridized probes with the theoretical hybridization pattern (i.e. the hybridization pattern expected for a wild-type sample).

Another object of the invention is concerns a method for in vitro detection of large rearrangement in the BRCA1 gene which comprises:
contacting the nucleic acid representative of chromosomal nucleic acid comprising the target amplified sequence, in particular nucleic acid of human chromosome 17, in particular genomic DNA, of the biological sample, with one or several set(s) of amplification primers wherein the primers have a nucleotide sequence selected as follows:
one forward primer (oriented from telomere to centromere) located preferentially less than 5 kb, more preferentially less than 2 kb, even more preferentially less than 1 kb and even more preferentially less than 500 bp from the breakpoint location in the BRCA1 gene (i.e. between genomic positions 41,279,990 and 41,284,990; preferentially between positions 41,279, 990 and 41,281,990; more preferentially between positions 41,279,990 and 41,280,990 and even more preferentially between positions 41,279,990 and 41,280, 490); and
one reverse primer (oriented from centromere to telomere)) located preferentially less than 5 kb, more preferentially less than 2 kb, even more preferentially less than 1 kb and even more preferentially less than 500 bp from the breakpoint location in the NBR2 gene (i.e. between genomic positions 41,267,683 and 41,272,683; preferentially between positions 41,270, 683 and 41,272,683; more preferentially between positions 41,271,683 and 41,272,683 and even more preferentially between positions 41,272,183 and 41,272, 683); and where
the forward primer is located upstream of the reverse primer, enabling PCR amplification or PCR-related amplification of the target amplified sequence extending from exon 2 of the BRCA1 gene to the 5' end of the NBR2 gene, detecting the PCR amplified nucleic acid fragments or PCR-related amplified nucleic acid fragments and optionally sequencing them.

A method for in vitro detection of large rearrangement in the BRCA1 gene involving PCR amplification or PCR-related amplification as defined above is in particular a method wherein the primer sets are selected in the group of primer pairs having nucleotide sequences designated as F7/R7 (SEQ ID No3/SEQ ID No. 4), F9/R8 (SEQ ID No. 5/SEQ ID No. 6), F1/R1 (SEQ ID No. 7/SEQ ID No. 8), F1/R2 (SEQ ID No. 7/SEQ ID No. 10), F1/R3 (SEQ ID No. 7/SEQ ID No. 12), F2/R7 (SEQ ID No. 9/SEQ ID No. 4), F3/R4 (SEQ ID No. 11/SEQ ID No. 14), F3/R7 (SEQ ID No. 11/SEQ ID No. 4), F4/R7 (SEQ ID No. 13/SEQ ID No. 4), F5/R2 (SEQ ID No. 15/SEQ ID No. 10), F5/R3 (SEQ ID No. 15/SEQ ID No. 12), F6/R3 (SEQ ID No. 16/SEQ ID No. 12), F7/R1 (SEQ ID No. 3/SEQ ID No. 8), and F7/R2 (SEQ ID No. 9/SEQ ID No. 10) F7/R3 (SEQ ID No. 3/SEQ ID No. 12) wherein the "F" primer is a forward primer and the "R" primer is a reverse primer or are selected in the group of primer pairs constituted by the reverse complementary sequences of the above sequences in the primer pairs.

In a particular embodiment of the method for in vitro detection of large rearrangement in the BRCA1 gene involving PCR amplification or PCR-related amplification as defined herein, the primer sets are selected in the group of primer pairs having nucleotide sequences designated as F7/R7 (SEQ ID No3/SEQ ID No. 4), and F9/R8 (SEQ ID No. 5/SEQ ID No. 6) in the group of primer pairs constituted by the reverse complementary sequences of the above sequences in the primer pairs.

Based on the methods defined herein, the invention also relates to a method of in vitro determining predisposition to disease associated with amplification of sequences in the BRCA1 locus of human chromosome 17 in a biological sample obtained from a human patient, which comprises performing a method of detection of large rearrangement in the BRCA1 gene in said biological sample as defined herein.

In particular, such a method is a method for the determination of predisposition to breast cancer or ovarian cancer, wherein said predisposition is acknowledged when an amplification, especially a triplication of the target amplified sequence is observed.

In a further embodiment the invention concerns a method of determining or adapting medical follow-up and/or treatment of a breast cancer or an ovarian cancer, which comprises performing a method of detection of large rearrangement in the BRCA1 gene in said biological sample as defined herein.

The invention also concerns a primer pair wherein the forward and the reverse primers have respectively a sequence selected from:
- for the forward primer (oriented from telomere to centromere) a sequence located preferentially less than 5 kb, more preferentially less than 2 kb, even more preferentially less than 1 kb and even more preferentially less than 500 bp from the breakpoint location in the BRCA1 gene (i.e. between genomic positions 41,279,990 and 41,284,990; preferentially between positions 41,279,990 and 41,281,990; more preferentially between positions 41,279,990 and 41,280,990 and even more preferentially between positions 41,279,990 and 41,280,490); and
- for the reverse primer (oriented from centromere to telomere)) a sequence located preferentially less than 5 kb, more preferentially less than 2 kb, even more preferentially less than 1 kb and even more preferentially less than 500 bp from the breakpoint location in the NBR2 gene (i.e. between genomic positions 41,267,683 and 41,272,683; preferentially between positions 41,270,683 and 41,272,683; more preferentially between positions 41,271,683 and 41,272,683 and even more preferentially between positions 41,272,183 and 41,272,683). A primer pair selected from the group of primer pairs having nucleotide sequences F1/R1 (SEQ ID No. 7/SEQ ID No. 8), F1/R2 (SEQ ID No. 7/SEQ ID No. 10), F1/R3 (SEQ ID No. 7/SEQ ID No. 12), F2/R7 (SEQ ID No. 9/SEQ ID No. 4), F5/R2 (SEQ ID No. 15/SEQ ID No. 10), F5/R3 (SEQ ID No. 15/SEQ ID No. 12), F6/R3 (SEQ ID No. 16/SEQ ID No. 12) and F7/R2 (SEQ ID No. 9/SEQ ID No. 10) or in the group of primer pairs constituted by the reverse complementary sequences of the above sequences in the primer pairs.

The invention also concerns a mixture of probes comprising at least two labeled polynucleotides wherein each of the polynucleotides has a nucleotide sequence hybridizing with a nucleic acid sequence from the region extending from intron 2 of the BRCA1 gene to the NBR2 gene in human chromosome 17 and wherein each polynucleotide is labeled with a different visually detectable label.

In a particular mixture of polynucleotide probes of the invention, the polynucleotides have a nucleic acid sequence selected in the group of Synt1 (SEQ ID No. 1) and S7 (SEQ ID No. 2). The invention also relates to a kit for the detection of multiple copies of an amplified sequence having a size in a range of 6 kb to 8 kb and extending from intron 2 of the BRCA1 gene to the NBR2 gene in the human 17 chromosome in a biological sample comprising:
- a primer pair selected from the group of primer pairs having nucleotide sequences F1/R1 (SEQ ID No. 7/SEQ ID No. 8), F1/R2 (SEQ ID No. 7/SEQ ID No. 10), F1/R3 (SEQ ID No. 7/SEQ ID No. 12), F2/R7 (SEQ ID No. 9/SEQ ID No. 4), F5/R2 (SEQ ID No. 15/SEQ ID No. 10), F5/R3 (SEQ ID No. 15/SEQ ID No. 12), F6/R3 (SEQ ID No. 16/SEQ ID No. 12) and F7/R2 (SEQ ID No. 9/SEQ ID No. 10);
- optionally, a detection probe for the PCR-amplified nucleotide fragments, reagents for conducting PCR amplification or PCR-type amplification;
- instructions for use and packaging material.

Another object of the invention is an isolated polynucleotide comprising at least two or at least three tandem copies of a sequence, each copy having a size in a range of 6 kb to 8 kb and corresponding to a sequence extending from intron 2 of BRCA1 to the NBR2 gene in the human 17 chromosome.

Further aspects and characteristics of the invention are disclosed in the examples and in the figures.

EXAMPLES

1. Materials and Methods
Preliminary Patient Screening
Total human genomic DNA was obtained from the EBV-immortalized lymphoblastoid cell lines nr.10799001, 38 and 40 obtained from the Institut Curie (Paris), Preliminary screening for large rearrangements was performed with the QMPSF assay (Quantitative Multiplex PCR of Short Fluorescent Fragments) in the conditions described by Casilli et al and Tournier et al (Casilli et al., 2002) and by MLPA (Multiplex Ligation-Dependent Probe Amplification) using the SALSA MLPA kits P002 (MRC Holland, Amsterdam, The Netherlands) for BRCA1 and P045 (MRC-Holland) for BRCA2. The patient gave his written consent for BRCA1 analysis.

Molecular Combing
Sample Preparation
Total human genomic DNA was obtained from EBV-immortalized lymphoblastoid cell lines. A 45-µL suspension of 106 cells in PBS was mixed with an equal volume of 1.2% Nusieve GTG agarose (Lonza, Basel, Switzerland) prepared in 1×PBS, previously equilibrated at 50° C. The plugs were left to solidify for 30 min at 4° C., then cell membranes are solubilised and proteins digested by an overnight incubation at 50° C. in 250 µL of 0.5 M EDTA pH 8.0, 1% Sarkosyl (Sigma-Aldrich, Saint Louis, Mo., USA) and 2 mg/mL proteinase K (Eurobio, Les Ulis, France), and the plugs were washed three times at room temperature in 10 mM Tris, 1 mM EDTA pH 8.0. The plugs were then either stored at 4° C. in 0.5 M EDTA pH 8.0 or used immediately. Stored plugs were washed three times for 30 minutes in 10 mM Tris, 1 mM EDTA pH 8.0 prior to use.

Probe Preparation
All BRCA1 probes were cloned into pCR2.1-Topo or pCR-XL-Topo (Invitrogen) plasmids by TOPO cloning, using PCR amplicons as inserts. Amplicons were obtained using bacterial artificial chromosomes (BACs) as template DNA. For BRCA, the 207-kb BAC RP11-831F13 (ch17: 41172482-41379594, InVitrogen, USA) was used for probe cloning. Whole plasmids were used as templates for probe labelling by random priming. Briefly, for biotin (Biot) labeling, 200 ng of template was labelled with the DNA Bioprime kit (Invitrogen) following the manufacturer's instructions, in an overnight labelling reaction. For Alexa-488 (A488) or digoxigenin (Dig) labeling, the same kit and protocol were used, but the dNTP mixture was modified to include the relevant labeled dNTP, namely Dig-11-dUTP (Roche Diagnostics, Meylan, France) or A488-7-OBEA-dCTP (Invitrogen) and its unlabelled equivalent, both at 100 µM, and all other dNTPs at 200 µM. Labelled probes were stored at 20° C. For each coverslip, 5 µL of each labelled probe (⅒th of a labelling reaction product) was mixed with 10 µg of human Cot 1 and 10 µg of herring sperm DNA (both from Invitrogen) and precipitated in ethanol. The pellet was then resuspended in 22 µL of 50% formamide, 30% Blocking Aid (Invitrogen), 1×SSC, 2.5% Sarkosyl, 0.25% SDS, and 5 mM NaCl.

Synt1: the Synt1 probe described herein is the result of a PCR amplification using BAC RP11-831F13 as a template and the two following primers: Synt1-F (TTCAGAAAATA- CATCACCCAAGTTC) (SEQ ID NO:17) and Synt1-R (TACCATTGCCTCTTACCCACAA) (SEQ ID NO: 18). The predicted sequence of the Synt1 probe is as follows (corresponding to genomic coordinates 41,269,785-41,274,269):

(SEQ ID NO: 1)
TTCAGAAAATACATCACCCAAGTTCCCATCCCTACCTGTCTATCCACAAA
ACCAAGGCATTCCTGAGATTAGTTCATTTATTATACTAATATAACAAGTG
TTTATTAAGTATCTACTACTATATTCAAGTACTATTCTAGGAGATAGAAA
TGTAGCAGTTTACAAAATAAAGCCTGCTCTCATAGAGCTCATATTCTAGT
GTGGTAGACAGTTGATACGGAATTAAAGAATACATGGGAATAAGTGCATT
AAAGAGAAAAATTAAGCAGGGTAAGGGGAAACAGGTAGTTCAATATCTAT
GTGGGGGTGAGATGTACATGGGGGAGTCAGGAAAGGTTTCACTGAGGTG
AGACTAGAGGATAGCTTAATAATGTAAAGAAACACACTATGCAACAATTA
GGGGAAGAGCATTCCAAGAAAGAGGGAGCAGAGAAGGCAAACCCTGAGCA
GGACCATGCCTGTGTATGCAGGACATCAGATAGGTCAAGGTGCTAAAATG
TAATAATCCAGGAGGATATTGTAGGGAAAGACTATCAGAGAGGTAGCTGG
TAACTTCTGGTAGGAACCTATAGGCTATTTTAAATCTTTAGCTTTATTCT
GGTCTTTTTAATTTTCTTTTTTTTTTTCAGACAGAGTCTCGTTCTGTCGC
CCAGGCTGGAGTGCAGTGGCACCATCTCGGCTCTCTGTAACCTCCGCCTC
CTGAATTCAAGTGATTCTCCTGCCTCAGCCTCCCGAGTAGCTGGGACTAA
AGGCATGCACCACCATGCCTTGGCCTCCCAAAGTACTGGGATTACAGGAG
TGAGCCACCATGCCAGCCATCTTTTTAATTTTTAATGTTAATTAATTTTT
GTAGAGACAGGATCTCACTATGATGCCCATGCTGGTCTTGAATGCCTGGC
ATCAAGCAATCTTCCTGCTTCGGCTTCCCAAAGTGCTGGGATTACAGGTG
TGAGCTACTATACCCGGCCTTTAGCTTTCTTCTGAATGTGAACCTTTTTT
TTTTTTTTTGGAGATGGAGTCTCACTCACTCTGCTGCTCAGGCTGGAGTG
CAGTGGTGTGGTCTTGGCTCACTGCAACCTCTGCCTCTCGGATTGAAGTG
ATTCTTGTGCCTCAGCATTCCAAGTAGCTGGGACTACAGGCGCGTGCTGC
CACACCCGGCTAATTTTTTTGTATTTTTGGTAGGGAAGGGGTTTCACCAT
ATTGCCCAGGCTGGTCTTGAAGTCCTGACCTCAAGTGATCCATCTGCCTC
GACCGGGATTACAGGCGTGAGCCACTACACTTAGCTCTAAATGTGAATTT
TTGAAACGGATTTTTTGGATAAAGTCCAGGCAAGATATCAAAGAACGACT
AACCTGGCAGTGTGACAAGAATGTGGTTTTTTCCTTAAATATTTAACTTT
TTAGAAAAGGATCACAAGGGCCAGGTGCGGTGGCTCACGCTGTAATCCCA
GCATTTTGGGAGGCCAAGGCGGGCAGCCTGGGTGACAGAGAATCCATCT
CAAAAAAGAAAAAAAAAAAGAAAAGGATCACAAGAAAAGCTTGTGGAC
AGTAACCTTATTGTGAAGGGTTGTAATACAACTCTTGTAATCATGGGGTT
TTTGACATAGCACAGGGCAGTGAAAAGAAAAACAATGAACTAAGTCAGGA
GGCTGGGTTTCTACTACCAGTTGTGTATATAAGCAGAGCCACCTTGGGCT
AACCACTCTACCTGAACCTGTTTCCTTCTCTTGCCATTCACCCTGCCAGA
CTCCTTGGGCTATTGCAAGAATAAAATTAAATGCTACTTGGGAAAATGCT
TCACAACCTGAGATGACTTGGGAAAAATGCTTCACAACCTGAGATAACTT

GTACCAACATTGGTATTATTACTGGGACCAAATGTGACTTTAAAAGAAA
AACAACCTTGACAAAGAAAACTCTGATTGGTTACTAAATCCCTATTTCTG
AGATAAGCTACATTTCAAAGAAATTCTCCGTAAAAGAAAAATTGGATTCA
GTTATCATACCAGATGGCTTTCATTCTCACCACTGACTCAATTCTGAAAC
AATTATATTTCAGTATGGTAATTATAATCTAAACTATATAAACACACTGT
AAACACAAACTTTGAACAGATGAAAACTCCGATATGTAAAAAGGTAATGA
ATGTTGAAGGAAGACTGTGAAAAGGGAAAAGAAAAAAAATTAAAATGTTC
CCCTTCTAGGTCCTGATGAGAGTAAATGTTTACTATAAAAATGATTCAAA
TATTTTAAACACTTTTCAAACCAGGCAATATTTTAGGCCTACTGTATATT
TGCATTTTGAGCTTCCAATACGGATAAGTGACTGGAAAAAGCAGCTAGGT
TTAGGTTGAAAAACAACAACCCACCGGGGAACACATTTTAGCAAATTCTT
CTGAAAGTCAAAAATGTTATAGTCATAGGTAAAAAGTTACAAAGAACTAC
CAATTGTCAGAAATAGCTGCCAATATTGACTTAGAAGACAGCAGAAGGAA
TTTTAGTTCAAGAAACCTAAAACAGGCTGAAAACCTTACCTACCCTATAG
CTACCACAAATAACACTGTTTCCAGTCATGATCATTCCTGATCACATATT
AAGACATAACTGCAAATTGTGCTATACTGTACTATATTAAAAGGAAGTGA
AATATGATCCCTATCCTAGAACTTTCCATACAAATGAATGTAAAACACCA
TAAAAATTAATCTTAAGGCCGGGCGCGGTGGCTCACGCCTGTAATCCCAG
CACTTTGGGAGGCCGAGGTGGGCGGATCACGAGGTCAGGAAGTGGAGACC
ATCCTGGCTAACACGGTGAAACCCCGTCTCTACTAAAAATACAAAAAATT
AGCCGGGCGTGGTGGTGGACGCCTGTAGTCCCAGCTACTTGGGGGGCCGA
GGCAGGAGAATGGCGTGAACCCGGGAGGCGGAGCTTGCAGTGAGCCGAGA
TGGCGCCACTGCACTCCGGCCTGGGTGAAAGAGCGAGACTCCGTCTCAAA
AACAAAACAAACAAAAATTAATCTTAAGCCAGGCGCAGTGGCTCACGCCA
GCACTTTGGAAGGCCGAGGCGGGTGGATCACGAGATCAGGACTTCAAGAC
CAGCCTGACCAACGTGATGAAACCCTATCTCTACTAAAAATACAAAATTA
GCCGGCCACGGTGGCGTGCGCCTATAATCCCAGCTACTCAGGAGGCTGAG
GCAGGAGAAGCGCTTGAACTTGAACCTGGCAGGCGGAGGTTGCAGTGAGC
CAAGATGGCGCCACTGCACTCCAGCCTGGGCGACAGAGCCAGACTCCAAC
CCCCCACCCCGAAAAAAAAAGGTCCAGGCCGGGCGCAGTGGCTCAGGACT
GTAATCCCAGCACTTTGGAAGGCTGAGGCGGGTGGATCACAAGGTCAGGA
GATCGAGACCATCTTGGCTAACATGGTGAAACCCCGTCTCTACTAAAAAT
ACAAAAATTAGCCGGGCATAGTGGTGGGCGCCTGTAGTCCCAGCTACTC
GGGAGGCTGAGGCAGGAGAATGGCCTGAACCCGGGAGGCGGAGCTGGCAG
TGAGCCAAGATCGTGCCACTGCACTCCAGCCTAGGCAGCAGAGCGAGACC
GTGTCTCAAAAAAACAAACAAACAAACAAAAGTCTGGGAGCGGTGG
CTCACGCCTGTAATCCCAGCACTTTCGGAGGCCAAGGCAGGAGGATCACC
TGAGGTCAGGAGTTCGAGACCAACCTGACCAATATGGAGAAACCCTGTCT
CTACTAAAAATACAAAATTAGCTGGTGTGATGGCACATGCCTGCAATCCC
AGGTACTCCGGAGGCTGAGGCAGCAGAATTGCTTGAACCCGGGAGGTGGA

-continued
GGTTGTAGTGAGCCGAGATTGTGCCACTGCACTCCAGCCTGGGCAACAAG

AGCCAAAGTCTGTCTCAAAAAAAAAAAAAAAAAAAAAAAAAGAAATTAAT

CTTAACAGGAAACAGAAAAAAGCAATGAAAAGCTAGAAAACATAATAGTT

GATTGAAAATAACAATTTAGCATTTTCATTCTTACATCTTTAATTTTTAT

GTATCTGAGTTTTTAATTGATGGTTTAATTTGCCAGAATGAGAAAGAACA

TCCTATTTTTATGACTCTCTCCCATGGAAATGAAACATAAATGTATCCAA

ATGCCACACTATTGAGGATTTTCCTGATCACTGATTGTCATGAGTAAGTT

TTGTGCTTTTTCAAAAGCAGTTTTTTCCTACAATGTCATTTCCTGCTTCT

CTGGCTCTGATTTTCAATAAATTGATAAATTGTGAATCCTGTTTTCCTCT

TATTTTTGTTTAGCTATAATGTTGAAGGGCAAGGGAGAGGATGGTTATTT

ATAAATCTTGTATCGCTCTGAAAACACAACATACATTTTCCTTAATCTGA

TTAACTTGACTTCAAATATGAAAAACAACTTTCATAAAGCAGAAAAGAAT

TTACCCTTTTTTATTGTGGGTAAGAGGCAATGGTA

S7: the S7 probe described herein is the result of a PCR amplification using BAC RP11-831F13 as a template and primers corresponding to the reference human genome sequence at positions 41,275,399 (forward primer: GAGTT-TAGCTCTGTCGCTGGA) (SEQ ID NO:19) and 41,278,707 (reverse primer: TGCTAGCACGTTGTCACCTC) (SEQ ID NO:20). The predicted sequence of the S7 probe is as follows (corresponding to genomic coordinates 41275399-41278707):

(SEQ ID NO: 2)
AGTTTAGCTCTGTCGCTGGAGTTCAGTGGTGCCATATTGGCTCACAGCAA

CATCTGCCTCCTGGTTCAAGTGATTCTCCTGCCTCAGCCTCCTGAGTAGC

TGGGATTACAGGCACATGCCACTACGCCCAGCTAATTTTTGTATTTTTAG

TGGAGAGGGGGTTTCACCATGTTGGCCAGGATGGTCTCGATCTCCTGACC

TCGTGATCCTACCACCTTGGCCTCCCAAAGTGCTGGGATTACAGGCATAA

GCCACCGCCCTCGGCCTCATCCATGATTTTATTTTGCCATTTCAAGTGAT

GGAGCTTGTTTTAGAGCTGGAAGAAAAGCCAAAATGCCAGTTAATCTAAA

CTAGATTCCTGCCCCAGTGCAGAACCAATCAAGACAGAGTCCCTGTCTTT

CCCGGACCACAGGATTTGTGTTGAAAAGGAGAGGAGTGGGAGAGGCAGAG

TGGATGGAGAACAAGGAATCATTTTCTATATTTTAAAGTTCTTCAGTTA

AGAAAATCAGCAATTACAATAGCCTAATCTTACTAGACATGTCTTTTCTT

CCCTAGTATGTAAGGTCAATTCTGTTCATTTGCATAGGAGATAATCATAG

GAATCCCAAATTAATACACTCTTGTGCTGACTTACCAGATGGGACACTCT

AAGATTTTCTGCATAGCATTAATGACATTTTGTACTTCTTCAACGCGAAG

AGCAGATAAATCCATTTCTTTCTGTTCCAATGAACTTTAACACATTAGAA

AAACATATATATATATCTTTTTAAAAGGTTTATAAAATGACAACTTCATT

TTATCATTTTAAAATAAAGTAAATTTAAGATTTGGAAGGTTTTAGAATAA

TACAAACCAAAGAACTAATGACAACGTCCTTTATTTTTAAAGATTCTAGA

AGTTGCTTTTTGTAATTAGACAACATAAATTCTGAATTTTTTCACATATT

GCTGCCAACCCCTTGGGTCTTTTCCTTTCTCCAAGAAAGAGAAAGCTACA

GAGGAGTGACTGACCGGGTAGGTGGTGGTAGCCTTAGCTTTCTCCAATGT

-continued
TTCTGGTTGTTTTCTTTTTCTTGCATAAAACCAAAATCAACAACGACCAA

ACCAACACCAATCAAGGCCTCCCCGCCCCTAACCTTTCCCAGTGACCTGC

TCTCATCTCTGGATCCTCCTCAAGCACATCCCTGCCGGCAGCATCTGTTA

CTACTGACGCTCCTCTACTTCCCTCTTGCGCTTTCTCAATGGCGCAAATG

GATCCAGTTCTTAAGTTCTCCCTCCCACAAAATCCTGTCTCCTCCCCTTC

CCAGACATATTCCTGGCACCTCTTCTTCCACAAGGTCCCATCCTCTCATA

CATACCAGCCGGTGTTTTTTGTTTTGTTTTGTTTTGTTTTGTTTTGAGAC

AGTCTCGCTCTGTCGCCCAGGCTGGAGTGCAATGGCGCGATCTCGGCTCA

CTGCAACCTCCGCCTCCCGGGTTCTAGCGATTCTCCTGCCTCAGCCTCCT

GAGTAGCTGGAGCGGCACCACGCCCGGCTAATTTTTGTATTTTTAGTAGA

GACGGAGTTTCACCACGTTGGTCAGGCTGGTCTGGAACTCCTGACCTCAT

GACCAGCCGACGTTTTTAAAGACATAGTGTCCCCCTCAAGGCATATTCCA

GTTCCTATCACGAGGATTCCCCCACGGACACTCAGTGCCCCCTTCCTGAT

CCTCAGCGCTTCCCTCGCGACCTACAAACTGCCCCCCTCCCCAGGGTTCA

CAACGCCTTACGCCTCTCAGGTTCCGCCCCTACCCCCCGTCAAAGAATAC

CCATCTGTCAGCTTCGGAAATCCACTCTCCCACGCCAGTACCCCAGAGCA

TCACTTGGGCCCCCTGTCCCTTTCCCGGGACTCTACTACCTTTACCCAGA

GCAGAGGGTGAAGGCCTCCTGAGCGCAGGGGCCCAGTTATCTGAGAAACC

CCACAGCCTGTCCCCGTCCAGGAAGTCTCAGCGAGCTCACGCCGCGCAG

TCGCAGTTTTAATTTATCTGTAATTCCCGCGCTTTTCCGTTGCCACGGAA

ACCAAGGGGCTACCGCTAAGCAGCAGCCTCTCAGAATACGAAATCAAGGT

ACAATCAGAGGATGGGAGGGACAGAAAGAGCCAAGCGTCTCTCGGGGCTC

TGGATTGGCCACCCAGTCTGCCCCCGGATGACGTAAAAGGAAAGAGACGG

AAGAGGAAGAATTCTACCTGAGTTTGCCATAAAGTGCCTGCCCTCTAGCC

TCTACTCTTCCAGTTGCGGCTTATTGCATCACAGTAATTGCTGTACGAAG

GTCAGAATCGCTACCTATTGTCCAAAGCAGTCGTAAGAAGAGGTCCCAAT

CCCCCACTCTTTCCGCCCTAATGGAGGTCTCCAGTTTCGGTAAATATAAG

TAATAAGGATTGTTGGGGGGTGGAGGGAAATAATTATTTCCAGCATGCG

TTGCGGAATGAAAGGTCTTCGCCACAGTGTTCCTTAGAAACTGTAGTCTT

ATGGAGAGGAACATCCAATACCAGAGCGGGCACAATTCTCACGGAAATCC

AGTGGATAGATTGGAGACCTGTGCGCGCTTGTACTTGTCAACAGTTATGG

ACTGGAGTGTTATGTTTTCGTATTTTGAAAGCAGAAACTAGGCCTTAAAA

AGATACGTACAACTCTTTAGGGAGACTACAATTCCCATCCAGCCCCAGGA

GTCTGGGGCAAGTAGTCTTGTAAGGTCAGTGGCCTGCGGGGACGCAGTGA

GCGCCGAATTTGCCTGGGCAGGGAAATGCGCTCTGGCCCATGTCTGCG

CACTCGTAGTTCCACCCCTCAGCCCCAGTGTTTGTTATTTTTCGGGTTCA

GCTTGCTTTTGCCCCGTCTCCGTCGACGCAATCGCCACCAGTCAATGGGG

TGGTCGTTTTGAGGGACAAGTGGTAAGAGCCAATCTTCTTGGCGAAAACG

CGGAGAAACGGGACTAGTTACTGTCTTTGTCCGCCATGTTAGATTCACCC

CACAGAGATAGCGGCAGAGCTGGCAGCGGACGGTCTTTGCATTGCCGCCT

-continued

```
CCCCAGGGGGCGGGAAGCTGGTAAGGAAGCAGCCTGGGTTAGCTAGGGGT

GGGGTCACGTCACACTAAGAGGGTTTGGAGAAGTTCAAGGGAGGAATCCT

GCAAAGAAGAGGGGCGACTTTTTCCGTGTCTCCGGACAGCTAATCGTTTT

AGTGACAGGATGAGAGAGCCCTTCGTGTTCTGAGGGACCGAGTGGGCGAA

AAGCGCCGGAGAGTTGGAGAGTCTGTGGTTCAGAATGCGAGGTGACAACG

TGCTAGCAG
```

Genomic DNA Combing and Probe Hybridisation

Genomic DNA was stained by 1 h incubation in 40 mM Tris, 2 mM EDTA containing 3 µM Yoyo-1 (Invitrogen, Carlsbad, Calif., USA) in the dark at room temperature. The plug was then transferred to 1 mL of 0.5 M MES pH 5.5, incubated at 68° C. for 20 min to melt the agarose, and then incubated at 42° C. overnight with 1.5 U beta agarase I (New England Biolabs, Ipswich, Mass., USA). The solution was transferred to a combing vessel already containing 1 Ml of 0.5 M MES pH 5.5, and DNA combing was performed with the Molecular Combing System on dedicated coverslips (Combicoverslips) (both from Genomic Vision, Paris, France). Combicoverslips with combed DNA are then baked for 4 h at 60° C. The coverslips were either stored at −20° C. or used immediately for hybridisation. The quality of combing (linearity and density of DNA molecules) was estimated under an epi-fluorescence microscope equipped with an FITC filter set and a 40× air objective. A freshly combed coverslip is mounted in 20 µL of a 1 ml ProLong-gold solution containing 1 µL of Yoyo-1 solution (both from Invitrogen) Prior to hybridisation, the coverslips were dehydrated by successive 3 minutes incubations in 70%, 90% and 100% ethanol baths and then air-dried for 10 min at room temperature. The probe mix (20 µL; see Probe Preparation) was spread on the coverslip, and then left to denature for 5 min at 90° C. and to hybridise overnight at 37° C. in a hybridizer (Dako). The coverslip was washed three times for 5 mM in 50% formamide, 1×SSC, then 3×3 min in 2×SSC. Detection was performed with two or three successive layers of flurorophore or streptavidin-conjugated antibodies, depending on the modified nucleotide employed in the random priming reaction (see above). For the detection of biotin labelled probes the antibodies used were Streptavidin-A594 (InVitrogen, Molecular Probes) for the 1st and 3rd layer, biotinylated goat anti-Streptavidin (Vector Laboratories) for the 2nd layer; For the detection of A488-labelled probes the antibodies used were rabbit anti-A488 (InVitrogen, Molecular Probes) for the 1st and goat anti-rabbit A488 (InVitrogen, Molecular Probes) for the 2nd layer; For the detection of digoxygenin labelled probes the antibodies used were mouse anti-Dig (Jackson Immunoresearch) for the 1st layer, rat anti-mouse AMCA (Jackson Immunoresearch) for the 2nd layer and goat anti-mouse A350 (InVitrogen, Molecular Probes) for the 3rd Layer. We performed a 20 minutes incubation step at 37° C. in a humid chamber for each layer, and three successive 3 minutes washes in 2×SSC, 0.1% Tween at room temperature between layers. Three additional 3 minutes washes in PBS and dehydration by successive 3 minutes washes in 70%, 90% and 100% ethanol were performed before mounting the coverslip.

Image Acquisition

Image acquisition was performed with a customized automated fluorescence microscope (Image Xpress Micro, Molecular Devices, Sunnyvale, Calif., USA) at 40.times. magnification, and image analysis and signal measurement were performed with the softwares ImagaJ and JMeasure (Genomic Vision, Paris, France). Hybridisation signals corresponding to the BRCA1 probes were selected by an operator on the basis of specific patterns made by the succession of probes. For all motifs signals belonging to the same DNA fiber, the operator identified the ends of each segment and determined its identity and length (kb), on a 1:1 scale image. The data were then output in a spreadsheet. In the final analysis, only intact signals were considered, i.e. signals where no fiber breakage had occurred within the BRCA1 motifs.

Statistical Analysis

Molecular Combing allows DNA molecules to be stretched uniformly with a stretching factor close to 2 kb/µm (Michalet et al., 1997). For each motif, the following values were determined: the number of measured images (n), the theoretical calculated length (in kb), the mean measured length (kb), the standard deviation (sd, in kb), the coefficient of variation (CV, in %), the difference between measured and calculated length (delta, in kb).

2. Results

Design of the High-Resolution BRCA1 Genomic Morse Code v4.0

An electronic reconstruction of the designed BRCA1 GMC v4.0 is shown in FIG. 1. The BRCA1 GMC covers a region of 200 kb, including the upstream genes NBR1, NBR2, LOC100133166, and TMEM106A, as well as the pseudogene BRCA1P1. The complete BRCA1 GMC is composed of 14 signals, and to facilitate GMC recognition and measurement, signals on the BRCA1+ NBR2 genes were grouped together in 8 specific patterns called "motifs" (m1b1-m8b1).

Characterization by Molecular Combing of a Novel Tandem Repeat Triplication of Exons 1a, 1b and 2 in BRCA1

Figure 2:
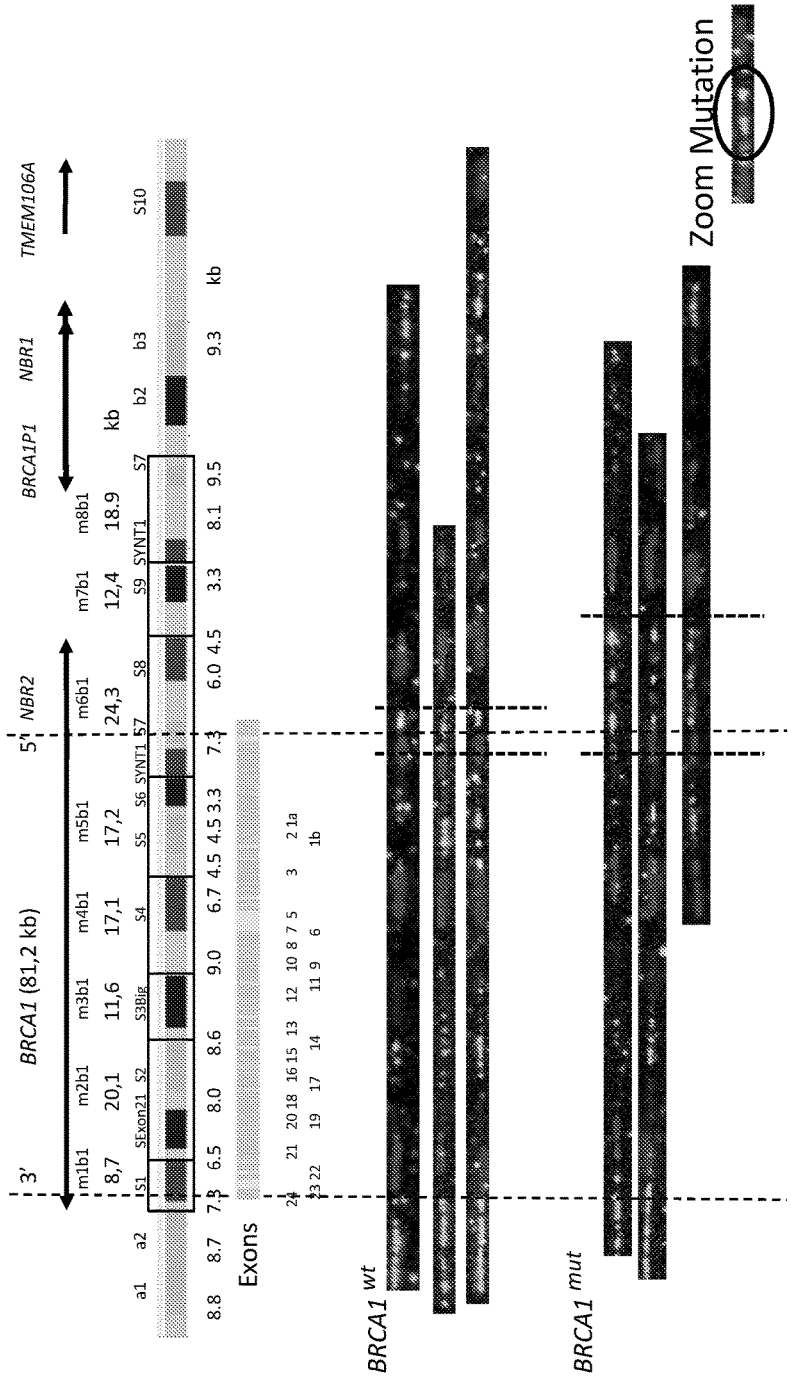
FIG. 2: Molecular Combing analysis of breast cancer cell-line 10799001.
DNA isolated from EBV-immortalized B lymphocytes (cell-line 10799001) co d from a breast cancer patient was analyzed by Molecular Combing.
(A) BRCA1 v 4.0 GMC computer simulation is shown at the top, the BRCA1 signals obtained after microscopic visualization are shown at the bottom. 3 microscopy signals are shown for each allele.
A triplication, visible as a tandem repeat triplication of the signal SYNT1 and the signal S7. The position of the detected triplication is indicated with vertical dotted lines. wt=wild type allele; mut=mutated allele bearing triplication.
(B) Same as (A), but with a different color for DNA probe S7, to confirm the nature of the probe involved in the mutation.

The presence of a large rearrangement on BRCA1 was first identified by visual inspection of the hybridization signals. A fraction of the detected signals showed a hybridization pattern differing from the normal pattern by the presence, between the S7 and S8 probe signals, of two additional pairs of signals corresponding to the color of the Synt1 and S7 probes (FIG. 2A). The signals were shown to arise from these probes by color swapping experiments, where the colors of some probes in the GMC are modified so as to observe the corresponding change in the hybridization signals. In one experiment, for example, the 87 probe was changed from green to blue and this resulted in the same change of color of the duplicated signal (FIG. 2B). The duplicated signal for the 87 probe was found to correspond to the full length of the 87 probe, while the additional signals for the Synt1 probe were found to correspond to only part of the Synt1 probe. This indicated the presence of a mutated allele, carrying an amplification of a region extending from the Synt1 probe to the gap between the S7 and S8 probes, along with an unmodified, wild-type allele in this sample.

Measurements were performed independently on signals from both alleles, the signals being attributed to either allele by the operator based on the hybridization pattern.

In one experiment, the SF was established from measurements of unmodified motifs (either from the wild-type allele or from unmodified regions in the mutated allele) to be 1.8 kb/µm. In the mutated allele, the distance from Synt1 to 88 was measured to be 38.5 kb, 14.9 kb longer than the expected size of 23.6 kb for a wild-type allele. This is expected to correspond to the measurement of the two extra copies of the amplified sequence, and the amplified sequence was thus determined to measure 7.4 kb. The 95% confidence interval for the size, calculated as 7.4 kb+/−

2.sd√n (where n is the number of measurements used in the calculation), was found to be 6.6 kb-8.2 kb.

In another experiment, the size of the first and second additional pairs of signals corresponding to Synt1 and S7 were measured to be 6.6 kb and 7.0 kb, respectively (from one end of the additional Synt1 probe signal to the other end of the proximal S7 probe signal) and the size of the region spanning both pairs of additional signals was measured to be 14.2 kb (from one end of the first additional Synt1 probe signal to the other end of the second additional S7 probe). Measuring the pairs of signals possibly excludes part of the amplified sequence (the part comprised between the S7 probe and the S8 probe) and was therefore considered an underestimate of the amplified sequence. The difference between the sum of both pairs measured individually and the direct measurement of the region spanning both pairs is a measurement of the part of the amplified sequence comprised between the S7 and S8 probes. This was measured to be 0.64 kb on average with a 95% confidence interval, calculated as above, of 0.2 kb-1.1 kb.

The 95% confidence interval as above for the size of the region spanning both pairs measured directly, defined as above, is 13.4 kb-14.9 kb. This measurement corresponds to two copies of the amplified sequence, with the exclusion of one copy of the part of the amplified sequence comprised between the S7 and 88 probes. The 95% confidence interval for the size of the amplified sequence, when accounting for the part excluded from measurements using the determination above, is therefore 6.8 kb-8.0 kb.

Here, we report the identification and characterization of a triplication of a 6 kb-8.0 kb sequence, extending from intron 2 of the BRCA1 gene to the NBR2 gene. One extremity of the amplified sequence is within 2 kb of the extremity of the 87 probe (thus within genomic coordinates 41,278,700-41,280,700 in build hg19), while the other, as determined from the size of the amplified sequence is within genomic coordinates 41,270,700-41,274,700 in build hg19. This is the first report of a genomic amplification in this Alu-rich 5'-region of BRCA1, and the mutation is the second triplication reported so far in BRCA1. (Horgervost Cancer Research 2003, Sluiter Breast Cancer Research 2011).

3. Breakpoint Characterization of the BRCA1 Triplication by PCR and Sequencing

Based on our estimation of the location of the breakpoint, we designed PCR primer pairs in order to specifically amplify the sequence containing the breakpoint in the sample with the triplication.

PCR Amplification

PCR and were performed in 50 μL reactions. Cycling conditions were chosen according to the polymerase and the length of the sequence to amplify. The Taq polymerase Expand High Fidelity from Roche was employed using following PCR conditions for each reaction: 200 μM dNTP, 300 μM primers, 1.5 mM MgCl2, 2.6 U Taq. PCR amplification conditions were for the primer pairs F7/R7 and F9/R8: 10 cycles of (94° C. for 15 s, 57° C. for 30 s, 72° C. for 2 min), 30 cycles of (94° C. for 15 s, 57° C. for 30 s, 72° C. for 2 min), 72° C. for 7 min; for the other primer pairs: 95° C. for 5 min, 30 cycles of (94° C. for 30 s, 60° C. for 60 s, 72° C. for 1 min), 72° C. for 10 min. PCR products were analyzed on a 1% agarose gel containing SYBRsafe (InVitrogen) with 1 μg of the Marker Hyperladder 1 (Promega).

Primers have been designed with the Primer3 v.04.0 software and synthesized by MWG/Eurogentec. Primer sequences and temperature of annealing are the following:

F7 5'-AGGGTTTCATCACGTTGGTC-3' 58° C., (SEQ ID NO: 3)

R7 5'-GCAAATGTAGTGGGGACTTG-3' 57° C., (SEQ ID NO: 4)

F9 5'-CTGCGCCTGGCTTAAGAT-3' 57° C., (SEQ ID NO: 5)

R8 5'-GATGTGGGTGGGGTCAGA-3' 58° C., (SEQ ID NO: 6)

F1 5'-ATAGGGTTTCATCACGTTGGTC-3' 60° C., (SEQ ID NO: 7)

R1 5'-CTAATCTGGTGGGCACTTGG-3' 60° C., (SEQ ID NO: 8)

F2 5'-GTCTTGAAGTCCTGATCTCGTG-3' 59° C., (SEQ ID NO: 9)

R2 5'-GTGTCTAGCTTGGGGTTTGG-3' 60° C., (SEQ ID NO: 10)

F3 5'-GAGATAGGGTTTCATCACGTTG-3' 59° C., (SEQ ID NO: 11)

R3 5'-CAGATGGGGACTTGGAAAAC-3' 59° C., (SEQ ID NO: 12)

F4 5'-GTTTCATCACGTTGGTCAGG-3' 59° C., (SEQ ID NO: 13)

R4 5'-CTGAGTCAGATGGGGACTTG-3' 58° C., (SEQ ID NO: 14)

F5 5'-GTTCAAGTTCAAGCGCTTCTC-3' 59° C., (SEQ ID NO: 15)

F6 5'-CTGCCAGGTTCAAGTTCAAG-3' 58° C. (SEQ ID NO: 16)

Following primers pairs were tested and validated by PCR: F7/R7 (SEQ ID No3/SEQ ID No. 4), F9/R8 (SEQ ID No. 5/SEQ ID No. 6), F1/R1 (SEQ ID No. 7/SEQ ID No. 8), F1/R2 (SEQ ID No. 7/SEQ ID No. 10), F1/R3 (SEQ ID No. 7/SEQ ID No. 12), F2/R7 (SEQ ID No. 9/SEQ ID No. 4), F3/R4 (SEQ ID No. 11/SEQ ID No. 14), F3/R7 (SEQ ID No. 11/SEQ ID No. 4), F4/R7 (SEQ ID No. 13/SEQ ID No. 4), F5/R2 (SEQ ID No. 15/SEQ ID No. 10), F5/R3 (SEQ ID No. 15/SEQ ID No. 12), F6/R3 (SEQ ID No. 16/SEQ ID No. 12), F7/R1 (SEQ ID No. 3/SEQ ID No. 8), and F7/R2 (SEQ ID No. 9/SEQ ID No. 10) F7/R3 (SEQ ID No. 3/SEQ ID No. 12).

DNA Gel Purification and Sequencing

PCR amplified DNA fragments were purified with the QIAquick kit (QIAGEN), according to manufacturer's instructions. Purified fragments were then sequenced by Sanger sequencing (Plate-forme de séquençage et génomique, Institut Cochin Paris). DNA sequences were then analysed with the biological sequence alignment editor BioEdit (http://www.mbio.ncsu.edu/bioedit/bioedit.html) and bioinformatics analysis was performed with the software BLAST (http://blast ncbi.nlm.nih.gov/Blast.cgi).

Results

Figure 3:
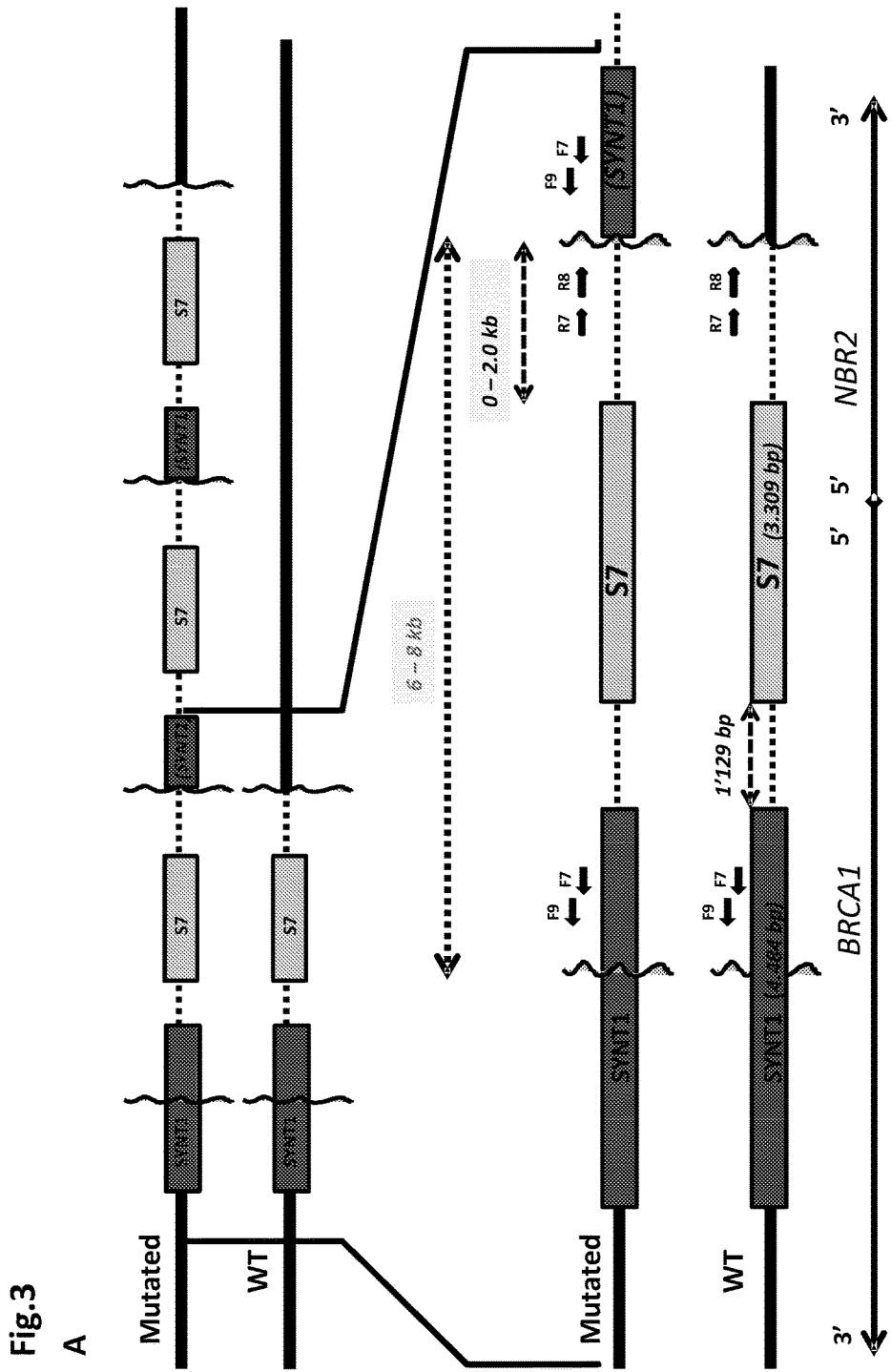
FIG. 3: Physical mapping of the Triplication of exons 1a, 1b and 2 in BRCA1. (A) Preliminary physical map derived by the Molecular Combing experiments and related measures. Above are the physical maps for the mutated allele (bearing the triplication) and the wild-type allele (corresponding to the reference human genome sequence), with a blown-up view below. The solid line represents the sequence left unchanged in the mutated allele, while the dotted line represents the sequence amplified in the mutated allele. The vertical wavy line is the estimated breakpoint position (and its replicates in the mutated allele). Synt1 and S7 designate full-length signals from the corresponding probes, while (Synt1) designates the partial signal arising from the Synt1 probe. Sizes indicated in by are the actual size of the probes and gap, while sizes in kb intervals are estimates from Molecular Combing experiments. Four primers are shown as representative examples of primer positioning for the amplification of the breakpoint. (B)-(C) DNA fragments derived after PCR performed in the cell-line 10799001 or the control cell-line 40.
Figure 3:
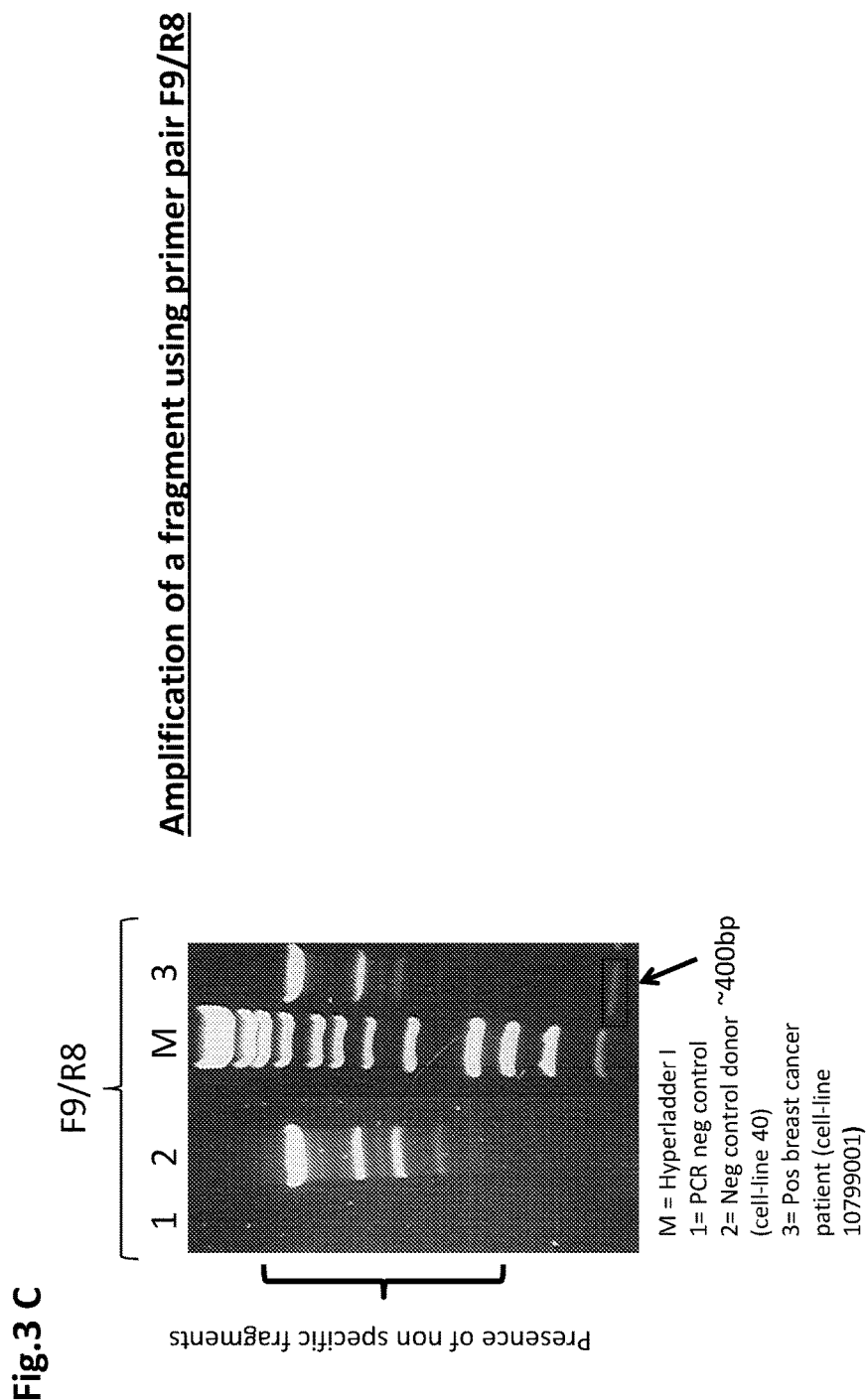

We were able to successfully amplify two DNA fragments by PCR, specific for the cell-line 10799001 bearing the BRCA1 triplication, but not for the control cell-line 40, employing primer pairs F7/R7 and F9/R8 (FIGS. 3B-3C). An apparent 600 bp DNA fragment was amplified by PCR with the primers F7/R7, and an apparent 400 pb DNA fragment with primers F9/R8. Sequencing of the fragments resulted in 574 (primer F7), 561 (primer R7), 337 (primer F9) and 306 (primer R8) bases long DNA fragments. Bioinformatics analysis confirmed that the DNA fragment amplified by primers F7/R7 and F9/R8 was identical, with the F9/R8 being shorter than the F7/R7 fragment.

Figure 4:
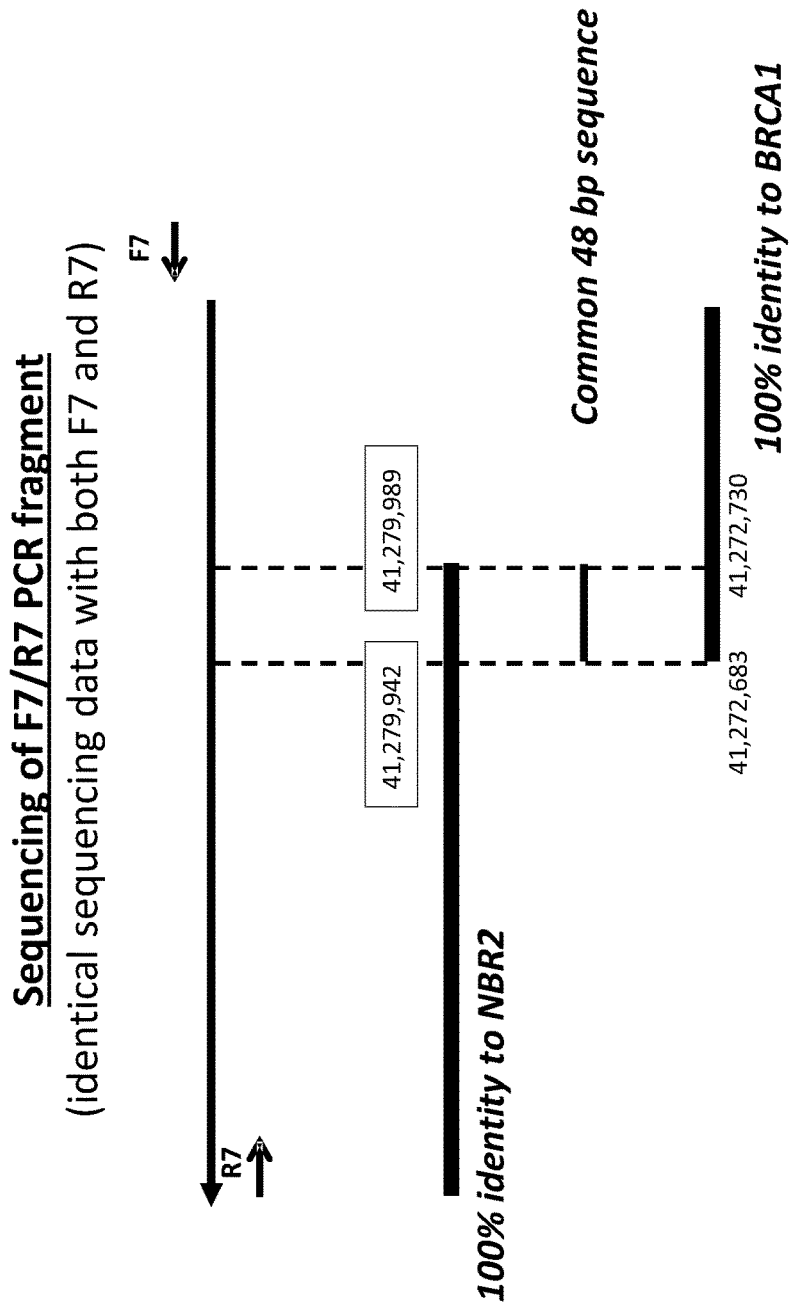
FIG. 4: Exact physical mapping of the BRCA1 triplication of exons 1a, 1b and 2. (A) Diagram showing results of breakpoint sequencing: sequence identity between sequence data from the F7R7 PCR fragment and the reference human genome sequence is depicted by horizontal bars, with corresponding genomic coordinates.

Sequence comparison with the reference human genome sequence showed that the amplified fragments were constituted by the region of intron 2 of BRCA1 extending from position 41,272,683 towards the telomere and the 5' region of NBR2 extending from position 41,279,989 towards the centromere connected by a 48 bp sequence common to both positions 41,272,683 in intron 2 of BRCA1 and 41,279,942, in the 5' region of NBR2 (FIG. 4). The 48 bp common sequence is as follows:

(SEQ ID NO: 21)
GAGGCAGGAGAATGGCGTGAACCCGGGAGGCGGAGCTTGCAGTGAGCC.

This is perfectly compatible with the triplication of the 7.3 kb-sequence fragment comprised between these two positions, with the breakpoint occurring in a stretch of perfect sequence identity Direct PCR Testing Since PCR amplification using primer pairs F7/R7 and F9/R8 resulted in the amplification of PCR products in a control sample without amplification, we designed additional primer pairs that amplify products specifically in the sample bearing the amplification reported here.

Figure 5:
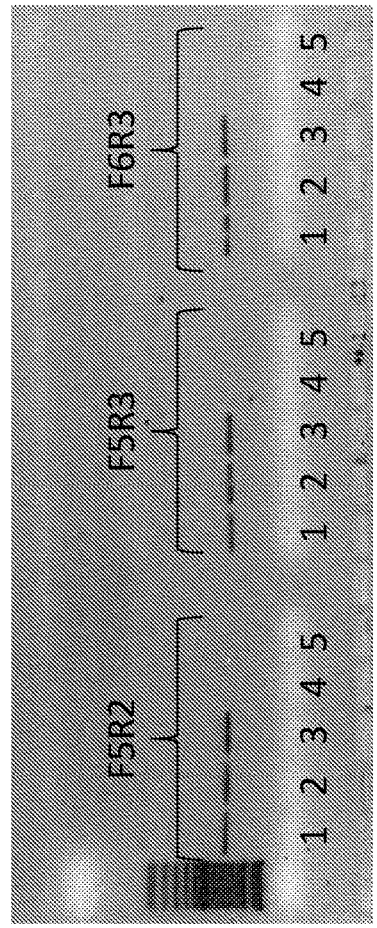
FIG. 5: Optimized PCR reaction to screen for the BRCA1 triplication in clinical samples. (A) Fragments specific for the BRCA1 triplication were obtained out 8 primers pairs. One single DNA fragment, without any disturbing unspecific fragments, was found for primer pairs F5/R2, F5/R3 and F6/R3 in the mutation positive cell-line 10799001, but not in the control cell-line 38. (B) Specific amplification of PCR fragments from primer pairs F5/R2, F5/R3 and F6/R3 observed in 3 unrelated patients harboring the amplification. No PCR product was observed for two negative controls.

As shown in FIG. 5A, fragments specific for the BRCA1 triplication were obtained out of 8 primer pairs (F1/R1, F1/R2, F1/R3, F2/R7, F5/R2, F5/R3, F6/R3, F7/R2), with sizes consistent with the relative location of the primers and breakpoints. Primer pairs F5/R2, F5/R3 and F6/R3 showed amplification products only in the mutation positive cell-line 10799001, but not in the control cell-line 38.

Additional samples, from three unrelated patients (coming from different French regions, also unrelated to the patient from whom cell line 10799001 was established) where an amplification had been suspected following aCGH testing, were submitted to PCR amplification with primer pairs F5/R2, F5/R3 and F6/R3. A specific PCR product was observed, with the expected size for the amplification reported here, which was not observed in control samples (FIG. 5B). These PCR products were sequenced and results were identical to cell-line 10799001. This confirmed the identical nature of the amplification, with the same breakpoint position, in four unrelated samples.

The primer pairs described here are examples of primer pairs that enable the specific detection of the reported breakpoint. Indeed, in a wild-type sample, the relative orientation of the forward and reverse primers of any of these pairs is such that no specific amplification is possible: the forward primer allows priming for a polymerization towards the centromere, while it is located upstream of the reverse primer. The tandem amplification brings an additional copy of the sequence corresponding to the forward primer (see FIG. 3). This additional copy being downstream of the reverse primer, the amplification of the sequence stretch between both primers becomes possible. Using such an approach, the man skilled in the art may design other primer pairs with equivalent properties. Such primer pairs must be constituted of one forward primer (oriented from telomere to centromere) located preferentially less than 5 kb, more preferentially less than 2 kb, even more preferentially less than 1 kb and even more preferentially less than 500 bp from the breakpoint location in the BRCA1 gene (i.e. between genomic positions 41,279,990 and 41,284,990; preferentially between positions 41,279,990 and 41,281,990; more preferentially between positions 41,279,990 and 41,280,990 and even more preferentially between positions 41,279,990 and 41,280,490); and one reverse primer (oriented from centromere to telomere)) located preferentially less than 5 kb, more preferentially less than 2 kb, even more preferentially less than 1 kb and even more preferentially less than 500 bp from the breakpoint location in the NBR2 gene (i.e. between genomic positions 41,267,683 and 41,272,683; preferentially between positions 41,270,683 and 41,272,683; more preferentially between positions 41,271,683 and 41,272,683 and even more preferentially between positions 41,272,183 and 41,272,683); where the forward primer is located upstream of the reverse primer.

Discussion

The amplification reported here is the first report of a sequence amplification in the region of BRCA1 comprising exons 1a, 1 b and 2 and the intervening introns, and the second triplication reported in the BRCA1 locus. Of note, this region of BRCA1 is very rich in repetitive sequences. The prior art relied on methods which have low detection capacity for such amplifications, either because they fail to cover regions rich in repetitive sequences, or because they fail to distinguish the copy number change induced by a triplication from that induced by a duplication.

Here, we show that using Molecular Combing or related direct mapping methods in such regions, it is possible to correctly detect and characterize such amplifications. The probe sets illustrated here are examples of probe sets which can be used for this purpose when using Molecular Combing. Adaptations of this design are possible and readily achievable by the man skilled in the art, whether for Molecular Combing or for related direct mapping methods. Using such methods, the amplification is typically detected either by a change in the succession of detected sequences or by an increase in length of the region of interest.

We also show that although in some regions such as the one involved in the triplication reported here, the presence of repetitive sequences makes specific PCR amplification challenging, with sufficient knowledge of the breakpoint location it is possible to obtain a product specific for the amplification. The nature of the product may be confirmed by sequencing, which unambiguously allows characterizing the resulting rearrangement.

The sufficient knowledge of the breakpoint location needed here may be obtained by careful analysis of mapping results obtained through Molecular Combing or related direct mapping methods.

In the case of the amplification of the region extending from intron 2 of BRCA1 to the 5' portion of NBR2 reported here, which appears to be a recurrent event, the amplification may be immediately characterized by using previously validated primer pairs, such as the ones we disclose here. Besides, the precise description of the breakpoint disclosed here would allow a man skilled in the art to use an alternative method (or PCR using different primer pairs) for the detection of this amplification.

In cases where such amplifications are reported to be recurrent, i.e. to occur in unrelated samples, systematic screening may also be considered. Direct testing for these recurrent amplifications without prior mapping is likely to efficiently reveal such an amplification in a sample.

The following numbered paragraphs represent various embodiments of the invention:

1. A method for in vitro detection of large rearrangement in the BRCA1 gene contained in nucleic acid of a biological sample comprising nucleic acid representative of chromosomal nucleic acid, in particular nucleic acid of human chromosome 17, comprising the step of detecting multiple copies of a target amplified sequence which is a sequence including exons 1a, 1b and 2 of the BRCA1 gene in the human 17 chromosome.

2. A method for in vitro detection of large rearrangement in the BRCA1 gene contained in nucleic acid of a biological sample comprising nucleic acid representative of chromosomal nucleic acid, in particular nucleic acid of human chromosome 17, comprising the step of detecting multiple copies of a target amplified sequence which is a sequence having a size in a range of 6 kb to 8 kb and extending from intron 2 of the BRCA1 gene to the 5' end of the NBR2 gene in the human 17 chromosome.

3. A method for in vitro detection of large rearrangement in the BRCA1 gene according to paragraph 1 or 2 which comprises steps of:
   providing the nucleic acid of the biological sample which comprises the target amplified sequence in conditions that enable hybridization with a probe or a set of probes, in particular providing the nucleic acid of the biological sample which comprises the target amplified sequence as isolated nucleic acid;
   contacting said provided nucleic acid with a probe or a set of probes in conditions enabling hybridization of the probe(s) with the target sequence, wherein each probe hybridizes with all or part of the amplified sequence extending from intron 2 of the BRCA1 gene to the 5' end of the NBR2 gene,
   detecting signals corresponding to hybridized probe(s), in particular by visualization.

4. A method for in vitro detection of large rearrangement in the BRCA1 gene according to any of paragraphs 1 to 3, where the detected amplified nucleic acid sequence is present in a copy number of at least 3 successive copies, in particular a copy number of 3 thereby characterizing a triplication in tandem of the target amplified sequence in the biological sample.

5. A method for in vitro detection of large rearrangement in the BRCA1 gene according to any of paragraphs 1 to 4, wherein the detection of multiple copies of the target amplified sequences comprises measuring the size of the nucleic acid sequence hybridized to the probe(s) and comparing said measured size to the size of the amplified sequence taken as a single copy which is in a range of 6 kb to 8 kb.

6. A method for in vitro detection of large rearrangement in the BRCA1 gene according to any of paragraphs 1 to 5, wherein the nucleic acid representative of chromosomal nucleic acid, in particular nucleic acid of human chromosome 17 is stretched prior to contacting with the probe(s).

7. A method for in vitro detection of large rearrangement in the BRCA1 gene according to any of paragraphs 1 to 6, wherein the target sequence consists of the sequence extending from position 41,272,683 to position 41,279,942 in human chromosome 17 or a sequence framed by nucleic acid sequences consisting of the 48 base pairs sequence at position 41,272,683 in the BRCA1 gene and the identical sequence in the NBR2 gene.

8. A method for in vitro detection of large rearrangement in the BRCA1 gene according to any of paragraphs 1 to 7 wherein the set of probes comprises or consists of a mixture of probes comprising Synt1 probe having a nucleic acid sequence base pairing with a genomic sequence starting with nucleotide at position 41,269,785 and ending with nucleotide at position 41,274,269 and S7 probe having a nucleic acid sequence base pairing with a genomic sequence starting with nucleotide at position 41,275,399 and ending with nucleotide at position 41,278,707, said probes being labeled with different markers or labels, in particular with a marker or label enabling visualization of a different color for each probe when detected.

9. A method for in vitro detection of large rearrangement in the BRCA1 gene according to paragraph 8 wherein the Synt1 probe has the sequence amplified by primers Synt1F (SEQ ID No. 17) and Synt1R (SEQ ID No. 18) on a nucleic acid representative of the human BRCA1 gene or has the sequence of SEQ ID No. 1 and the S7 probe has the sequence amplified by primers S7F (SEQ ID No. 19) and S7R (SEQ ID No. 20) on a nucleic acid representative of the human BRCA1 and NBR2 genes or has the sequence of SEQ ID No. 2.

10. A method for in vitro detection of large rearrangement in the BRCA1 gene according to any of paragraphs 1 to 9, which comprises the steps of:
    providing isolated nucleic acid representative of chromosomal nucleic acid that comprises the target amplified sequence, in particular isolated nucleic acid of human chromosome 17, in particular isolated genomic DNA of human chromosome 17 in a combing vessel;
    performing molecular combing on said nucleic acid; to stretch the nucleic acid and provide physical mapping of said stretched nucleic acid;
    contacting combed nucleic acid with a labeled probe or a set of probes wherein each of the probe hybridizes with a distinct region of the target amplified sequence and is labeled with a different label, in conditions enabling hybridization of the probes with the target amplified sequence;
    washing the reaction mixture after hybridization;
    detecting the signals corresponding to hybridized labeled probes.

11. A method for in vitro detection of large rearrangement in the BRCA1 gene according to any of paragraphs 1 to 10, wherein the detection of signals corresponding to hybridized labeled probes of a set of probes encompasses detecting hybridization patterns and determining the succession of hybridized probes, their identity and their length.

12. A method for in vitro detection of large rearrangement in the BRCA1 gene according to paragraph 11, which further comprises a step of comparing the detecting hybridization patterns reflecting the succession of hybridized probes with the theoretical hybridization pattern (i.e. the hybridization pattern expected for a wild-type sample).

13. A method for in vitro detection of large rearrangement in the BRCA1 gene according to any of paragraphs 1 to 4 which comprises:
    contacting the nucleic acid representative of chromosomal nucleic acid comprising the target amplified sequence, in particular nucleic acid of human chromosome 17, in particular genomic DNA, of the biological sample, with one or several set(s) of amplification primers wherein the primers have a nucleotide sequence selected as follows:
one forward primer (oriented from telomere to centromere) located preferentially less than 5 kb, more preferentially less than 2 kb, even more preferentially less than 1 kb and even more preferentially less than 500 bp from the breakpoint location in the BRCA1 gene (i.e. between genomic positions 41,279,990 and 41,284,990; preferentially between positions 41,279,990 and 41,281,990; more preferentially between positions 41,279,990 and 41,280,990 and even more preferentially between positions 41,279,990 and 41,280,490); and
one reverse primer (oriented from centromere to telomere)) located preferentially less than 5 kb, more preferentially less than 2 kb, even more preferentially less than 1 kb and even more preferentially less than 500 bp from the breakpoint location in the NBR2 gene (i.e. between genomic positions 41,267,683 and 41,272,683; preferentially between positions 41,270,683 and 41,272,683; more preferentially between positions 41,271,683 and 41,272,683 and even more preferentially between positions 41,272,183 and 41,272,683); and where
the forward primer is located upstream of the reverse primer,
enabling PCR amplification or PCR-related amplification of the target amplified sequence extending from exon 2 of the BRCA1 gene to the 5' end of the NBR2 gene,
detecting the PCR amplified nucleic acid fragments or PCR-related amplified nucleic acid fragments and optionally sequencing them.

14. A method for in vitro detection of large rearrangement in the BRCA1 gene according to paragraph 14 wherein the primer sets are selected in the group of primer pairs having nucleotide sequences designated as F7/R7 (SEQ ID No3/SEQ ID No. 4), F9/R8 (SEQ ID No. 5/SEQ ID No. 6), F1/R1 (SEQ ID No. 7/SEQ ID No. 8), F1/R2 (SEQ ID No. 7/SEQ ID No. 10), F1/R3 (SEQ ID No. 7/SEQ ID No. 12), F2/R7 (SEQ ID No. 9/SEQ ID No. 4), F3/R4 (SEQ ID No. 11/SEQ ID No. 14), F3/R7 (SEQ ID No. 11/SEQ ID No. 4), F4/R7 (SEQ ID No. 13/SEQ ID No. 4), F5/R2 (SEQ ID No. 15/SEQ ID No. 10), F5/R3 (SEQ ID No. 15/SEQ ID No. 12), F6/R3 (SEQ ID No. 16/SEQ ID No. 12), F7/R1 (SEQ ID No. 3/SEQ ID No. 8), and F7/R2 (SEQ ID No. 9/SEQ ID No. 10) F7/R3 (SEQ ID No. 3/SEQ ID No. 12) wherein the "F" primer is a forward primer and the "R" primer is a reverse primer or are selected in the group of primer pairs constituted by the reverse complementary sequences of the above sequences in the primer pairs.

15. A method for in vitro detection of large rearrangement in the BRCA1 gene according to paragraph 14 wherein the primer sets are selected in the group of primer pairs having nucleotide sequences designated as F7/R7 (SEQ ID No3/SEQ ID No. 4), and F9/R8 (SEQ ID No. 5/SEQ ID No. 6) in the group of primer pairs constituted by the reverse complementary sequences of the above sequences in the primer pairs.

16. A method of in vitro determining predisposition to disease associated with amplification of sequences in the BRCA1 locus of human chromosome 17 in a biological sample obtained from a human patient, which comprises performing a method of detection of large rearrangement in the BRCA1 gene in said biological sample according to any of paragraphs 1 to 16.

17. A method according to paragraph 17 for the determination of predisposition to breast cancer or ovarian cancer, wherein said predisposition is acknowledged when an amplification, especially a triplication of the target amplified sequence is observed.

18. A method of determining or adapting medical follow-up and/or treatment of a breast cancer or an ovarian cancer, which comprises performing a method of detection of large rearrangement in the BRCA1 gene in said biological sample according to any of paragraphs 1 to 17.

19. A primer pair wherein the forward and the reverse primers have respectively a sequence selected from:
for the forward primer (oriented from telomere to centromere) a sequence located preferentially less than 5 kb, more preferentially less than 2 kb, even more preferentially less than 1 kb and even more preferentially less than 500 bp from the breakpoint location in the BRCA1 gene (i.e. between genomic positions 41,279,990 and 41,284,990; preferentially between positions 41,279,990 and 41,281,990; more preferentially between positions 41,279,990 and 41,280,990 and even more preferentially between positions 41,279,990 and 41,280,490); and
or the reverse primer (oriented from centromere to telomere)) a sequence located preferentially less than 5 kb, more preferentially less than 2 kb, even more preferentially less than 1 kb and even more preferentially less than 500 bp from the breakpoint location in the NBR2 gene (i.e. between genomic positions 41,267,683 and 41,272,683; preferentially between positions 41,270,683 and 41,272,683; more preferentially between positions 41,271,683 and 41,272,683 and even more preferentially between positions 41,272,183 and 41,272,683). A primer pair selected from the group of primer pairs having nucleotide sequences F1/R1 (SEQ ID No. 7/SEQ ID No. 8), F1/R2 (SEQ ID No. 7/SEQ ID No. 10), F1/R3 (SEQ ID No. 7/SEQ ID No. 12), F2/R7 (SEQ ID No. 9/SEQ ID No. 4), F5/R2 (SEQ ID No. 15/SEQ ID No. 10), F5/R3 (SEQ ID No. 15/SEQ ID No. 12), F6/R3 (SEQ ID No. 16/SEQ ID No. 12) and F7/R2 (SEQ ID No. 9/SEQ ID No. 10) or in the group of primer pairs constituted by the reverse complementary sequences of the above sequences in the primer pairs.

20. A mixture of probes comprising at least two labeled polynucleotides wherein each of the polynucleotides has a nucleotide sequence hybridizing with a nucleic acid sequence from the region extending from intron 2 of the BRCA1 gene to the NBR2 gene in human chromosome 17 and wherein each polynucleotide is labeled with a different visually detectable label.

21. A mixture of polynucleotide probes according to paragraph 21, wherein the polynucleotides have a nucleic acid sequence selected in the group of Synt1 (SEQ ID No. 1) and S7 (SEQ ID No. 2).

22. A kit for the detection of multiple copies of an amplified sequence having a size in a range of 6 kb to 8 kb and extending from intron 2 of the BRCA1 gene to the NBR2 gene in the human 17 chromosome in a biological sample comprising:
a primer pair selected from the group of primer pairs having nucleotide sequences F1/R1 (SEQ ID No. 7/SEQ ID No. 8), F1/R2 (SEQ ID No. 7/SEQ ID No. 10), F1/R3 (SEQ ID No. 7/SEQ ID No. 12), F2/R7 (SEQ ID No. 9/SEQ ID No. 4), F5/R2 (SEQ ID No.

15/SEQ ID No. 10), F5/R3 (SEQ ID No. 15/SEQ ID No. 12), F6/R3 (SEQ ID No. 16/SEQ ID No. 12) and F7/R2 (SEQ ID No. 9/SEQ ID No. 10);

optionally, a detection probe for the PCR-amplified nucleotide fragments, reagents for conducting PCR amplification or PCR-type amplification;

instructions for use and packaging material.

23. An isolated polynucleotide comprising at least two or at least three tandem copies of a sequence, each copy having a size in a range of 6 kb to 8 kb and corresponding to a sequence extending from intron 2 of BRCA1 to the NBR2 gene in the human 17 chromosome.

REFERENCES

Casilli, F., Di Rocco, Z. C., Gad, S., Tournier, I., Stoppa-Lyonnet, D., Frebourg, I., and Tosi, M. (2002) Rapid detection of novel BRCA1 rearrangements in high-risk breast-ovarian cancer families using multiplex PCR of short fluorescent fragments. Hum Mutat 20, 218-226.

Dimalanta E T, Lim A, Runnheim R, Lamers C, Churas C, Forrest D K, de Pablo J J, Graham M D, Coppersmith S N, Goldstein S, Schwartz D C (2004). "A 75 microfluidic system for large DNA molecule arrays." Anal Chem. 2004 Sep. 15; 76(18):5293-301.

Florijn R J, Bonden L A, Vrolijk H, Wiegant J, Vaandrager J W, Baas F, den Dunnen J T, Tanke H J, van Ommen G J, Raap A K (1995). "High-resolution DNA Fiber-FISH for genomic DNA mapping and colour bar-coding of large genes." Hum Mol Genet. 1995 May; 4(5):831-6.

Fransz P F, Alonso-Blanco C, Liharska T B, Peeters A J, Zabel P, de Jong J H (1996). "High-resolution physical mapping in *Arabidopsis thaliana* and tomato by fluorescence in situ hybridization to extended DNA fibres." Plant J. 1996 March; 9(3):421-30.

Gad, S., Aurias, A., Puget, N., Mairal, A., Schurra, C., Montagna, M., Pages, S., Calm, V., Mazoyer, S., Bensimon, A., et al. (2001). Color bar coding the BRCA1 gene on combed DNA: a useful strategy for detecting large gene rearrangements. Genes Chromosomes Cancer 31, 75-84.

Gad, S., Bieche, I., Barrois, M., Casilli, F., Pages-Berhouet, S., Dehainault, C., Gauthier-Villars, M., Bensimon, A., Aurias, A., Lidereau, R., et al. (2003). Characterization of a 161 kb deletion extending from the NBR1 to the BRCA1 genes in a French breast-ovarian cancer family. Hum Mutat 21, 654.

Gad, S., Caux-Moncoutier, V., Pages-Berhouet, S., Gauthier-Villars, M., Coupier, I., Pujol, P., Frenay, M., Gilbert, B., Maugard, C., Bignon, Y. J., et al. (2002a). Significant contribution of large BRCA1 gene rearrangements in 120 French breast and ovarian cancer families. Oncogene 21, 6841-6847.

Gad, S., Klinger, M., Caux-Moncoutier, V., Pages-Berhouet, S., Gauthier-Villars, M., Coupier, I., Bensimon, A., Aurias, A., and Stoppa-Lyonnet, D. (2002b). Bar code screening on combed DNA for large rearrangements of the BRCA1 and BRCA2 genes in French breast cancer families. J Med Genet39, 817-821.

Gill P, Ghaemi A. Nucleic acid isothermal amplification technologies: a review. Nucleosides Nucleotides Nucleic Acids. 2008 March; 27(3):224-43.

Haaf T, Ward D C (1994). "Structural analysis of alpha-satellite DNA and centromere proteins using extended chromatin and chromosomes." Hum Mol Genet. 1994 May; 3(5):697-709.

Heiskanen M, Kallioniemi O, Palotie A (1996). "Fiber-FISH: experiences and a refined protocol." Genet Anal. 1996 March; 12(5-6):179-84.

Heiskanen M, Karhu R, Hellsten E, Peltonen L, Kallioniemi O P, Palotie A (1994). "High resolution mapping using fluorescence in situ hybridization to extended DNA fibers prepared from agarose-embedded cells." Biotechniques. 1994 November; 17(5):928-9, 932-3.

Heng H H, Squire J, Tsui L C (1992). "High-resolution mapping of mammalian 30 genes by in situ hybridization to free chromatin." Proc Natl Acad Sci USA. 1992 Oct. 15; 89(20):9509-13.

Herrick, J., and Bensimon, A. (2009). Introduction to molecular combing: genomics, DNA replication, and cancer. Methods Mol Biol 521, 71-101.

Hofmann, W., Wappenschmidt B., Berhane, S., Schmutzler, R., and Scherneck, S. (2002). Detection of large rearrangements of exons 13 and 22 in the BRCA1 gene in German families. Med Genet 39, E36.

Hogervorst F B, Nederlof P M, Gille J J, McElgunn C J, Grippeling M, Pruntel R, Regnerus R, van Welsem T, van Spaendonk R, Menko F H, Kluijt I, Dommering C, Verhoef S, Schouten J P, van't Veer L J, Pals G (2003). Large genomic deletions and duplications in the BRCA1 gene identified by a novel quantitative method. Cancer Res. 2003 Apr. 1; 63(7):1449-53.

Jing J, Reed J, Huang J, Hu X, Clarke V, Edington J, Housman D, Anantharaman T S, Huff E J, Mishra B, Porter B, Shenker A, Wolfson E, Hiort C, Kantor R, Aston C, Schwartz D C (1998). "Automated high resolution optical mapping using arrayed, fluid-fixed DNA molecules." Proc Natl Acad Sci USA. 1998 Jul. 7; 95(14): 8046-51.

King, M. C., Marks, J. H., and Mandell, J. B. (2003). Breast and ovarian cancer risks due to inherited mutations in BRCA1 and BRCA2. Science 302, 643-646.

Larson J W, Yantz G R, Zhong Q, Charnas R, D'Antoni C M, Gallo M V, Gillis K A, Neely L A, Phillips K M, Wong G G, Gullans S R, Gilmanshin R (2006). "Single DNA molecule stretching in sudden mixed shear and elongational microflows." Lab Chip. 2006 September; 6(9): 1187-99. Epub 2006 Jul. 7.

Mann S M, Burkin D J, Grin D K, Ferguson-Smith M A (1997). "A fast, novel approach for DNA fibre-fluorescence in situ hybridization analysis." Chromosome Res. 1997 April; 5(2):145-7.

Mazoyer, S. (2005). Genomic rearrangements in the BRCA1 and BRCA2 genes. Hum Mutat 25, 415-422.

Michalet X, Ekong R, Fougerousse F, Rousseaux S, Schurra C, Hornigold N, van Slegtenhorst M, Wolfe J, Povey S, Beckmann J S, Bensimon A (1997). "Dynamic molecular combing: stretching the whole human genome for high resolution studies." Science; 277(5331):1518-23.

Nathanson, K. L., Wooster; R., and Weber, B. L. (2001). Breast cancer genetics: what we know and what we need. Nat Med 7, 552-556.

Palotie A, Heiskanen M, Laan M, Horelli-Kuitunen N (1996). "High-resolution fluorescence in situ hybridization: a new approach in genome mapping." Ann Med. 1996 April; 28(2):101-6. 77 Parra I, Windle B (1993). "High resolution visual mapping of stretched DNA by fluorescent hybridization." Nat Genet. 1993 September; 5(1):17-21.

Raap A K (1998). "Advances in fluorescence in situ hybridization." Mutat Res. 1998 May 25; 400(1-2):287-98.

Rouleau, E., Lefol, C., Tozlu, S., Andrieu, C., Guy, C., Copigny, F., Nogues, C., Bieche, I., and Lidereau, R. (2007). High-resolution oligonucleotide array-CGH applied to the detection and characterization of large rearrangements in the hereditary breast cancer gene BRCA1, Clin Genet 72, 199-207.

Samad A, Huff E F, Cai W, Schwartz D C (1995). "Optical mapping: a novel, single-molecule approach to genomic analysis." Genome Res. 1995 August; 5(1):1-4.

Schouten J P, McElgunn C J, Waaijer R, Zwijnenburg D, Diepvens F, Pals G. Relative quantification of 40 nucleic acid sequences by multiplex ligation-dependent probe amplification. Nucleic Acids Res. 2002 Jun. 15; 30(12): e57

Schurra, C., and Bensimon, A. (2009). Combing genomic DNA for structural and functional studies. Methods Mol Biol 464, 71-90.

Schwartz D C, Li X, Hernandez L I, Ramnarain S P, Huff E J, Wang Y K (1996). "Ordered restriction maps of *Saccharomyces cerevisiae* chromosomes constructed by optical mapping." Science. 1993 Oct. 1; 262(5130):110-4.

Sluiter M D, van Rensburg E J (2011). Large genomic rearrangements of the BRCA1 and BRCA2 genes: review of the literature and report of a novel BRCA1 mutation. Breast Cancer Res Treat, 2011 January; 125(2):325-49. doi: 10.1007/s10549-010-0817-z. Epub 2010 Mar. 16.

Staaf, J., Torngren, T., Rambech, E., Johansson, U., Persson, C., Sellberg, G., Tellhed, L., Nilbert, M., and Borg, A. (2008). Detection and precise mapping of germline rearrangements in BRCA1, BRCA2, MSH2, and MLH1 using zoom-in array comparative genomic hybridization (aCGH). Hum Mutat 29, 555-564.

Szabo, C., Masiello, A., Ryan, J. F., and Brody, L. C. (2000). The breast cancer information core:database design, structure, and scope. Hum Mutat 16, 123-131.

Vaandrager J W, Schuuring E, Kluin-Nelemans H C, Dyer M J, Raap A K, Kluin P M (1996).

"DNA fiber fluorescence in situ hybridization analysis of immunoglobulin class switching in B-cell neoplasia: aberrant C H gene rearrangements in follicle center-cell lymphoma." Blood. 1998 Oct. 15; 92(8):2871-8.

van Binsbergen E. Origins and breakpoint analyses of copy number variations: up close and personal. Cytogenet Genome Res. 2011; 135(3-4):271-6. doi: 10.1159/000330267. Epub 2011 Aug. 12, Walsh, T., Lee, M. K., Casadei, S., Thornton, A. M., Stray, S. M., Pennil, C., Nord, A. S., Mandell, J. B., Swisher, E. M., and King, M. C. (2010). Detection of inherited mutations for breast and ovarian cancer using genomic capture and massively parallel sequencing. Proc Natl Acad Sci USA 107, 12629-12633.

Wiegant J, Kalle W, Mullenders L, Brookes S, Hoovers J M, Dauwerse J G, van Ommen G J, Raap A K (1996). "High-resolution in situ hybridization using DNA halo preparations." Hum Mol Genet. 1992 November; 1(8): 587-91.

Murphy P D, Allen A C, Alvares C P, Critz B S, Olson S J, Schelter D B, Zeng B: Coding sequences of the human BRCA1 gene U.S. Pat. No. 5,750,400 Skolnick M H, Goldgar D E, Miki Y, Swenson J, Kamb A, Harshman K D, Shattuck-eidens D M, Tavtigian S V, Wiseman R W, Futreal A P: 17q-linked breast and ovarian cancer susceptibility gene U.S. Pat. No. 5,710,001

---

The invention claimed is:

1. A method for in vitro detection of at least three successive copies of a target sequence in the BRCA1 gene contained in a nucleic acid of a biological sample comprising genomic nucleic acid of human chromosome 17,
wherein the target sequence is a sequence having a size in a range of 6 kb to 8 kb and extending from intron 2 of the BRCA1 gene to the 5' end of the NBR2 gene in the human chromosome 17, and wherein said method comprises:
(a) providing the nucleic acid of the biological sample which comprises the target sequence, optionally as isolated nucleic acid;
(b) hybridizing under stringent conditions said nucleic acid to a labeled probe or a set of labeled probes, wherein each labeled probe hybridizes with all or part of the sequence extending from intron 2 of the BRCA1 gene to the 5' end of the NBR2 gene;

wherein the labeled probe or the set of labeled probes is amplified by one or several set(s) of amplification primers having a nucleotide sequence selected as follows:
one forward primer (oriented from telomere to centromere) located between genomic positions 41,279,990 and 41,284,990 of the human reference genome sequence build GRCh37/hg19 of human chromosome 17; and
one reverse primer (oriented from centromere to telomere) located between genomic positions 41,267,683 and 41,272,683 of the human reference genome sequence build GRCh37/hg19 of human chromosome 17; and wherein
the forward primer is located upstream of the reverse primer, enabling PCR amplification or amplification by a PCR-related method of the target sequence;
(c) detecting signals corresponding to hybridized labeled probe(s);

(d) comparing the resulting hybridization pattern reflecting the succession of hybridized labeled probes with the hybridization pattern expected for a wild-type sample; and (e) when said resulting hybridization pattern contains additional signals consisting of or comprising at least three identical patterns when compared to said hybridization pattern expected for a wild-type sample, concluding that the biological sample contains at least three successive copies of the target sequence.

2. The method for in vitro detection of at least three successive copies of a target sequence in the BRCA1 gene according to claim 1, wherein the target sequence consists of the sequence extending from position 41,272,683 to position 41,279,942 of the human reference genome sequence build GRCh37/hg19 of human chromosome 17.

3. The method for in vitro detection of at least three successive copies of a target sequence in the BRCA1 gene according to claim 1 wherein the set of labeled probes comprises a Synt1 probe having a nucleic acid sequence base pairing with a genomic sequence starting with nucleotide at position 41,269,785 and ending with nucleotide at position 41,274,269 of the human reference genome sequence build GRCh37/hg 19 of human chromosome 17 and an S7 probe having a nucleic acid sequence base pairing with a genomic sequence starting with nucleotide at position 41,275,399 and ending with nucleotide at position 41,278,707 of the human reference genome sequence build GRCh37/hg19 of human chromosome 17, said probes being labeled with different markers or labels, said markers or labels optionally enabling visualization of a different color for each probe when detected.

4. The method for in vitro detection of at least three successive copies of a target sequence in the BRCA1 gene according to claim 3, wherein the sequence of the Synt1 probe is the sequence amplified by primers Synt1F with the sequence of SEQ ID NO: 17 and Synt1R with the sequence of SEQ ID NO: 18 on a genomic nucleic acid of the human BRCA1 gene or is the sequence of SEQ ID NO: 1 and wherein the sequence of the S7 probe is the sequence amplified by primers S7F with the sequence of SEQ ID NO: 19 and S7R with the sequence of SEQ ID NO: 20 on a genomic nucleic acid of the human BRCA1 and NBR2 genes or is the sequence of SEQ ID NO: 2.

5. The method for in vitro detection of at least three successive copies of a target sequence in the BRCA1 gene according to claim 1, wherein the genomic nucleic acid of human chromosome 17 is a genomic DNA isolated from the biological sample and wherein said method further comprises:
at (a), providing isolated genomic DNA of human chromosome 17 in a combing vessel;
before (b), performing molecular combing on said genomic DNA to stretch the genomic DNA and provide physical mapping of said stretched genomic DNA;
in (b), hybridizing combed genomic DNA with the labeled probe or the set of labeled probes wherein each of the probes hybridizes with a distinct region of the target sequence and is labeled with a different label, washing the reaction mixture after hybridization of (b).

6. The method for in vitro detection of at least three successive copies of a target sequence in the BRCA1 gene according to claim 5, wherein the detection of signals corresponding to hybridized labeled probes of a set of probes encompasses detecting hybridization patterns and determining the succession of hybridized probes, their identity and their length.

7. The method for in vitro detection of at least three successive copies of a target sequence in the BRCA1 gene according to claim 1 wherein the set of amplification primers is wherein the "F" primer is a forward primer and the "R" primer is a reverse primer, or is the pair of primers with reverse complementary sequences to the primers F5 and R2.

8. The method for in vitro detection of at least three successive copies of a target sequence in the BRCA1 gene according to claim 7, wherein the set of amplification primers further comprise primer pairs selected from the group of primer pairs having nucleotide sequences designated as F7/R7 (SEQ ID NO: 3/SEQ ID NO: 4), and F9/R8 (SEQ ID NO: 5/SEQ ID NO: 6), the pair of primers with reverse complementary sequences to the primers F7 and R7, and the pair of primers with reverse complementary sequences to the primers F8 and R8.

9. The method for in vitro detection of at least three successive copies of a target sequence in the BRCA1 gene according to claim 1, wherein said method further comprises a step of correlating the presence of at least three successive copies of the target sequence with a predisposition to a breast cancer.

10. The method for in vitro detection of at least three successive copies of a target sequence in the BRCA1 gene according to claim 1, wherein the set or sets of amplification primers are selected from the group of primer pairs having nucleotide sequences designated as F7/R7 (SEQ ID NO: 3/SEQ ID NO: 4), F9/R8 (SEQ ID NO: 5/SEQ ID NO: 6), F1/R1 (SEQ ID NO: 7/SEQ ID NO: 8), F1/R2 (SEQ ID NO: 7/SEQ ID NO: 10), F1/R3 (SEQ ID NO: 7/SEQ ID NO: 12), F2/R7 (SEQ ID NO: 9/SEQ ID NO: 4), F3/R4 (SEQ ID NO: 11/SEQ ID NO: 14), F3/R7 (SEQ ID NO: 11/SEQ ID NO: 4), F4/R7 (SEQ ID NO: 13/SEQ ID NO: 4), F5/R3 (SEQ ID NO: 15/SEQ ID NO: 12), F6/R3 (SEQ ID NO: 16/SEQ ID NO: 12), F7/R1 (SEQ ID NO: 3/SEQ ID NO: 8), and F7/R2 (SEQ ID NO: 9/SEQ ID NO: 10) F7/R3 (SEQ ID NO: 3/SEQ ID NO: 12), wherein the "F" primer is a forward primer and the "R" primer is a reverse primer, or are selected from the group consisting of the pairs of primers with reverse complementary sequences to the sequences in the primer pairs above.

11. A method for in vitro detection of at least three successive copies of a target sequence in the BRCA1 gene contained in a nucleic acid of a biological sample comprising genomic nucleic acid of human chromosome 17, wherein the target sequence is a sequence having a size in a range of 6 kb to 8 kb and extending from intron 2 of the BRCA1 gene to the 5' end of the NBR2 gene in the human chromosome 17, and wherein said method comprises the steps of:
(a) providing the nucleic acid of the biological sample which comprises the target sequence, optionally as isolated nucleic acid;
(b) hybridizing under stringent conditions said nucleic acid to a labeled probe or a set of labeled probes, wherein each labeled probe hybridizes with all or part of the sequence extending from intron 2 of the BRCA1 gene to the 5' end of the NBR2 gene;
wherein the labeled probe or the set of labeled probes is amplified by one or several set(s) of amplification primers having a nucleotide sequence selected as follows:
one forward primer (oriented from telomere to centromere) located between genomic positions 41,279,990 and 41,284,990 of the human reference genome sequence build GRCh37/hg19 of human chromosome 17; and one reverse primer (oriented from centromere to telomere) located between genomic positions 41,267,683 and 41,272,683 of the human reference genome sequence build GRCh37/hg19 of human chromosome 17; and wherein
the forward primer is located upstream of the reverse primer, enabling PCR amplification or amplification by a PCR-related method of the target sequence;
(c) detecting signals corresponding to hybridized labeled probe(s);
(d) measuring the size of the nucleic acid sequence hybridized to the labeled probe(s); and
(e) comparing said measured size to the size of the target sequence, wherein when said measured size is three times greater than the expected size of the target sequence, concluding that the sample contains at least three successive copies of the target sequence.

* * * * *